United States Patent
Vodnala et al.

(10) Patent No.: US 12,415,845 B2
(45) Date of Patent: Sep. 16, 2025

(54) METHODS OF PRODUCING T CELL POPULATIONS USING HYDROXYCITRIC ACID AND/OR A SALT THEREOF

(71) Applicant: The United States of America, as represented by the Secretary, Department of Health and Human Services, Bethesda, MD (US)

(72) Inventors: Suman Kumar Vodnala, Bethesda, MD (US); Nicholas P. Restifo, Chevy Chase, MD (US); Rigel J. Kishton, Columbia, MD (US); Robert L. Eil, Chapel Hill, NC (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1242 days.

(21) Appl. No.: 17/050,045

(22) PCT Filed: Apr. 22, 2019

(86) PCT No.: PCT/US2019/028513
§ 371 (c)(1),
(2) Date: Oct. 23, 2020

(87) PCT Pub. No.: WO2019/209715
PCT Pub. Date: Oct. 31, 2019

(65) Prior Publication Data
US 2021/0071141 A1    Mar. 11, 2021

Related U.S. Application Data

(60) Provisional application No. 62/661,941, filed on Apr. 24, 2018.

(51) Int. Cl.
| | | |
|---|---|---|
| C12N 5/0783 | (2010.01) | |
| A61K 35/17 | (2025.01) | |
| A61K 40/11 | (2025.01) | |
| A61K 40/42 | (2025.01) | |
| A61P 35/00 | (2006.01) | |
| C07K 14/725 | (2006.01) | |

(52) U.S. Cl.
CPC .......... C07K 14/7051 (2013.01); A61K 40/11 (2025.01); A61K 40/4273 (2025.01); A61P 35/00 (2018.01); C12N 5/0636 (2013.01); A61K 2239/31 (2023.05); A61K 2239/38 (2023.05); A61K 2239/57 (2023.05)

(58) Field of Classification Search
CPC ....... C12N 5/0636; A61P 35/00; A61K 35/17; C07K 14/7051
See application file for complete search history.

(56) References Cited

U.S. PATENT DOCUMENTS

| | | |
|---|---|---|
| 7,820,174 B2 | 10/2010 | Wang et al. |
| 7,915,036 B2 | 3/2011 | Morgan et al. |
| 8,034,334 B2 | 10/2011 | Dudley et al. |
| 8,088,379 B2 | 1/2012 | Robbins et al. |
| 8,216,565 B2 | 7/2012 | Restifo et al. |
| 8,383,099 B2 | 2/2013 | Dudley et al. |
| 8,465,743 B2 | 6/2013 | Rosenberg et al. |
| 8,785,601 B2 | 7/2014 | Rosenberg et al. |
| 9,266,960 B2 | 2/2016 | Morgan et al. |
| 9,345,748 B2 | 5/2016 | Morgan et al. |
| 9,359,447 B2 | 6/2016 | Feldman et al. |
| 9,487,573 B2 | 11/2016 | Parkhurst et al. |
| 9,765,342 B2 | 9/2017 | Kochenderfer |
| 9,790,282 B2 | 10/2017 | Orentas et al. |
| 9,822,162 B2 | 11/2017 | Hinrichs et al. |
| 9,868,774 B2 | 1/2018 | Orentas et al. |
| 9,879,065 B2 | 1/2018 | Robbins et al. |
| 2012/0244133 A1 | 9/2012 | Rosenberg et al. |
| 2014/0378389 A1 | 12/2014 | Robbins et al. |
| 2015/0299317 A1 | 10/2015 | Orentas et al. |
| 2016/0333422 A1 | 11/2016 | Feldman et al. |
| 2017/0145070 A1 | 5/2017 | Hinrichs et al. |
| 2017/0218042 A1 | 8/2017 | Tran et al. |
| 2017/0224800 A1 | 8/2017 | Tran et al. |

FOREIGN PATENT DOCUMENTS

| | | | |
|---|---|---|---|
| WO | WO-2016067968 A1 * | 5/2016 | ............ A61K 31/22 |
| WO | WO 2017/076602 A1 | 5/2017 | |
| WO | WO 2018/053233 A1 | 3/2018 | |

OTHER PUBLICATIONS

Rosenberg et al. Clin Cancer Res. 2011; 17(13): 4550-7. (Year: 2011).*
Boyum. Scand J Immunol. 1976;5(Suppl 5):9-15. (Year: 1976).*
Parkhurst et al., Molecular Therapy. 2011; 19(3): 620-626. (Year: 2011).*
Chuah et al. In Vitro and In Vivo Toxicity of Garcinia or Hydroxycitric Acid: A Review. Evidence-Based Complementary and Alternative Medicine. 2012, Article ID 197920, p. 1-12. (Year: 2012).*
Beltran-Debon et al., The aqueous extract of Hibiscus sabdariffa calices modulates the production of monocyte chemoattractant protein-1 in humans. Phytomedicine. 2010;17:186-191. (Year: 2010)*
Ghosh et al., "In Vitro Cyto-genotoxicity of Hydroxycitric Acid: A Weight-loss Dietary Supplement", *Journal of Exploratory Research in Pharmacology*, 2(2): 41-48 (2017).
Balmer et al., "Memory CD8+ T Cells Require Increased Concentrations of Acetate Induced by Stress for Optimal Function," *Immunity*, 44: 1312-1324 (2016).

(Continued)

*Primary Examiner* — Laura Schuberg
*Assistant Examiner* — Jianjian Zhu
(74) *Attorney, Agent, or Firm* — Leydig, Voit & Mayer, Ltd.

(57) ABSTRACT

Provided are methods of producing an isolated population of T cells, the method comprising culturing isolated T cells in vitro in the presence of hydroxycitric acid, and/or a salt thereof, wherein the salt is potassium hydroxycitrate or sodium hydroxycitrate. Also provided are related isolated populations of cells, pharmaceutical compositions, and methods of treating or preventing cancer in a mammal.

10 Claims, 22 Drawing Sheets

Specification includes a Sequence Listing.

(56) References Cited

OTHER PUBLICATIONS

Dewes, "Potassium Hydroxy Citrate Promotes Longevity and Efficacy of Anti-Tumor T cells for Adoptive Cell Therapy (ACT)," *NCI Technology Transfer Center*, Ref. No. E-094-2018 (2018).
Eil et al., "Ionic immune suppression within the tumour microenvironment limits T cell effector function," *Nature*, 537: 539-543 (2016).
European Patent Office, International Search Report in International Patent Application No. PCT/US2019/028513, mailed Sep. 17, 2019.
European Patent Office, Written Opinion in International Patent Application No. PCT/US2019/028513, mailed Sep. 17, 2019.
Galluzzi et al., "Acivating autophagy to potentiate immunogenic chemotherapy and radiation therapy," *Nature Reviews: Clinical Oncology*, 14: 247-258 (2017).
Garcia-Ramirez et al., "Modulation of Chromatin Folding by Histone Acetylation," *The Journal of Biological Chemistry*, 270(30): 17923-17928 (1995).
Gattinoni et al., "Paths to stemness: building the ultimate antitumour T cell," *Nat. Rev. Cancer*, 12(10): 671-684 (2012).
Gray et al., "Polycomb repressive complex 2-mediated chromatin repression guides effector $CD8^+$ T cell terminal differentiation and loss of multipotency," *Immunity*, 46(4): 596-608 (2017).
Guais et al., "Adding a combination of hydroxycitrate and lipoic acid (METABLOC™) to chemotherapy improves effectiveness against tumor development: experimental results and case report," *Invest. New Drugs*, 30: 200-211 (2012).
Mariño et al., "Regulation of Autophagy by Cytosolic Acetyl-Coenzyme A," *Molecular Cell*, 53: 710-725 (2014).
Krasteva et al., "In vitro primary sensitization of hapten-specific T cells by cultured human epidermal Langerhans cells—a screening predictive assay for contact sensitizers," *Clinical and Experimental Allergy*, 26: 563-570 (1996).
MacKensen et al., "Phase I Study of Adoptive T-Cell Therapy Using Antigen-Specific $CD8^+$ T Cells for the Treatment of Patients With Metastatic Melanoma," *Journal of Clinical Oncology*, 24(31): 5060-5069 (2006).
Peng et al., "Aerobic glycolysis promotes T helper 1 cell differentiation through an epigenetic mechanism," *Science*, 354(6311): 481-484 (2016).
Pietrocola et al., "Caloric Restriction Mimetics Enhance Anticancer Immunosurveillance," *Cancer Cell*, 30: 147-160 (2016).
Restifo et al., "Adoptive immunotherapy for cancer: harnessing the T cell response," *Nature Reviews: Immunology*, 12: 269-281 (2012).
Schwartz et al., "A combination of alpha lipoic acid and calcium hydroxycitrate is efficient against mouse cancer models: Preliminary results," *Oncology Reports*, 23: 1407-1416 (2010).
Tran et al., "Cancer Immunotherapy Based on Mutation-Specific CD4+ T Cells in a Patient with Epithelial Cancer," *Science*, 344(6184): 641-645 (2014).
Van Niekerk et al., "Enhanced Therapeutic Efficacy in Cancer Patients by Short-term Fasting: The Autophagy Connection," *Frontiers in Oncology*, 6: 242 (2016).
Vodnala et al., "T cell stemness and dysfunction in tumors are triggered by a common mechanism," *Science*, 363: 1417 (2019).
Wellen et al., "ATP-citrate lyase links cellular metabolism to histone acetylation," *Science*, 324(5930): 1076-1080 (2009).
Xu et al., "Autophagy is essential for effector CD8 T cell survival and memory formation," *Nat. Immunol.*, 15(12): 1152-1161 (2014).
Yee et al., "Adoptive T cell therapy using antigen-specific $CD8^+$ T cell clones for the treatment of patients with metastatic melanoma: In vivo persistence, migration, and antitumor effect of transferred T cells," *PNAS*, 99(25): 16168-16173 (2002).
Dudley et al., "Generation of Tumor-Infiltrating Lymphocyte Cultures for Use in Adoptive Transfer Therapy for Melanoma Patients", *Journal of Immunotherapy*, 26(4): 332-342 (2003).
Riddell et al., "The use of anti-CD-3 and anti-CD28 monoclonal antibodies to clone and expand human antigen-specific T cells", *Journal of Immunological Methods*, 128: 189-201 (1990).

\* cited by examiner

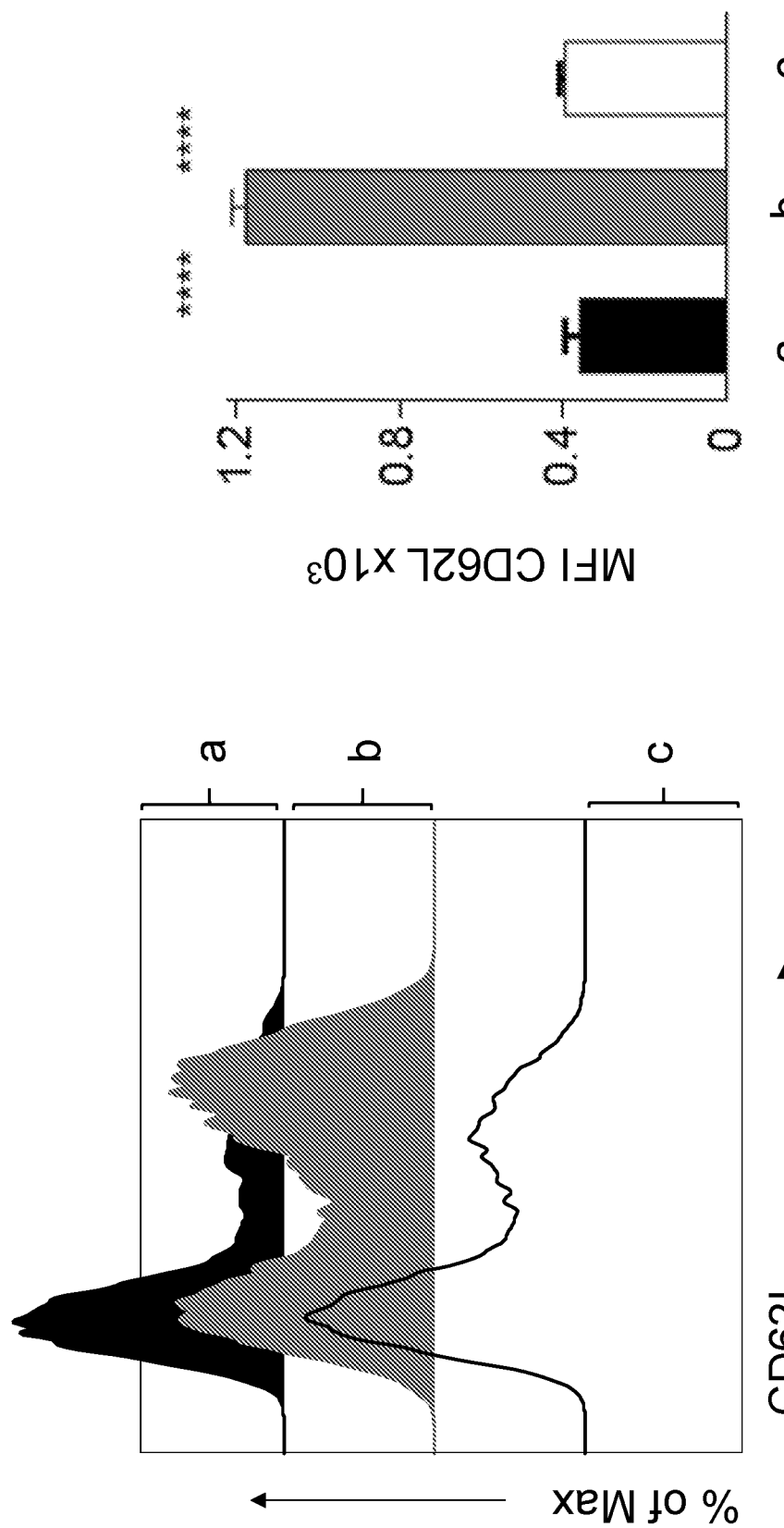

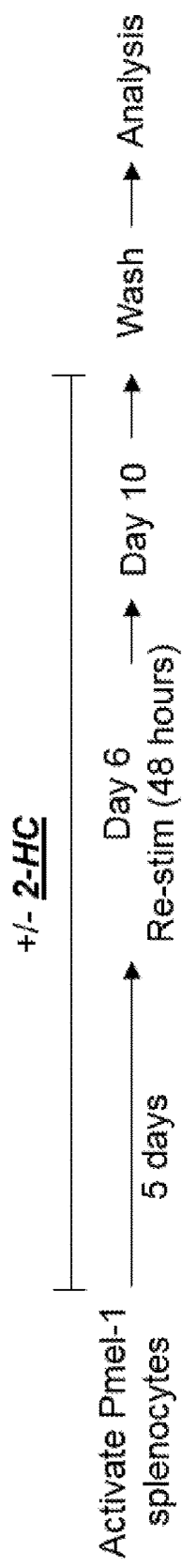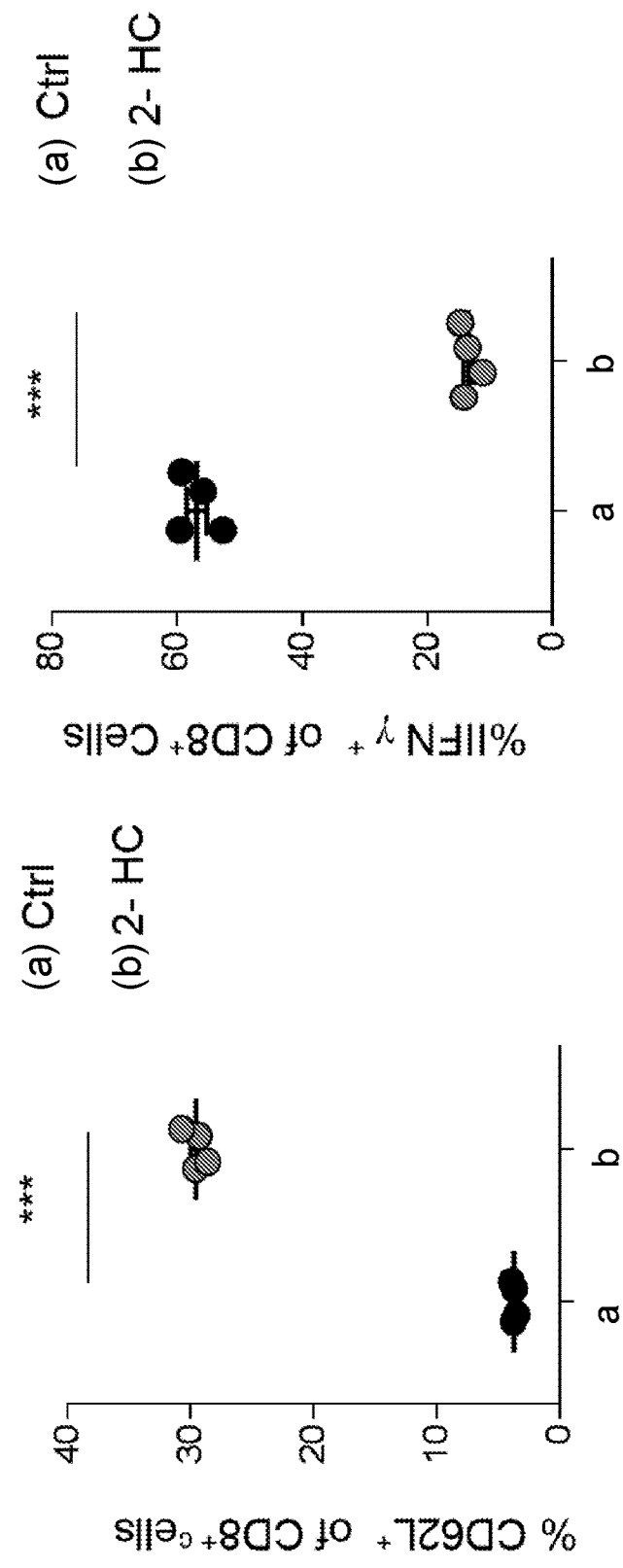
FIG. 7A
FIG. 7B
FIG. 7C

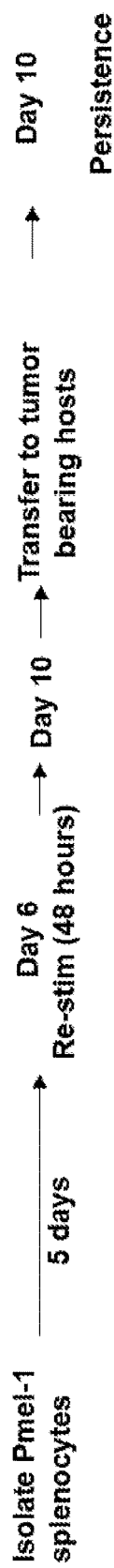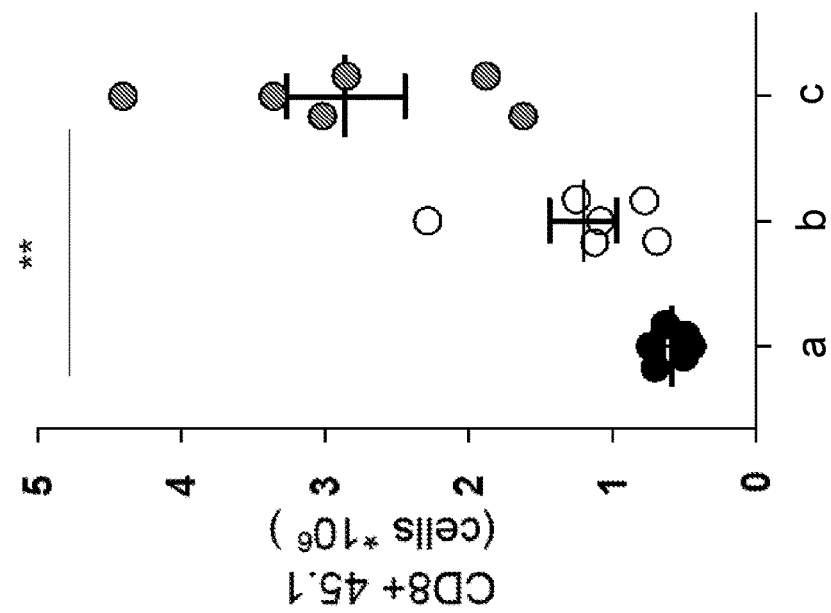
FIG. 15
FIG. 16

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: synthetic

<400> SEQUENCE: 1
ggagccttcg atcaggtata aa                                          22

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
ctcaagtcag agggtccaaa g                                           21

METHODS OF PRODUCING T CELL POPULATIONS USING HYDROXYCITRIC ACID AND/OR A SALT THEREOF

CROSS-REFERENCE TO RELATED APPLICATIONS

This patent application is a U.S. National Phase Patent Application of copending International Patent Application No. PCT/US2019/028513, filed Apr. 22, 2019, which claims the benefit of U.S. Provisional Patent Application No. 62/661,941, filed Apr. 24, 2018, both of which are hereby incorporated by reference in their entireties.

STATEMENT REGARDING FEDERALLY SPONSORED RESEARCH OR DEVELOPMENT

This invention was made with Government support under project number Z01ZIA BC010763-07 by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 786 Byte ASCII (Text) file named "750767_ST25.txt," dated Oct. 6, 2020.

BACKGROUND OF THE INVENTION

Adoptive cell therapy (ACT) using cancer-reactive T cells can produce positive clinical responses in some cancer patients. Nevertheless, several obstacles to the successful use of ACT for the treatment of cancer and other conditions remain. For example, one or more of the in vivo persistence, survival, and antitumor activity of T cells can, in some cases, decrease following adoptive transfer. Alternatively or additionally, in some cases, the increased apoptosis of T cells can pose obstacles to the treatment of cancer and other conditions. Accordingly, there is a need for methods of obtaining an improved isolated population of cells for ACT.

BRIEF SUMMARY OF THE INVENTION

An embodiment of the invention provides a method of producing an isolated population of T cells, the method comprising culturing isolated T cells in vitro in the presence of hydroxycitric acid, and/or a salt thereof, wherein the salt is potassium hydroxycitrate or sodium hydroxycitrate.

Another embodiment of the invention provides a method of administering T cells to a mammal, the method comprising culturing isolated T cells in vitro in the presence of a hydroxycitric acid, and/or a salt thereof, wherein the salt is potassium hydroxycitrate or sodium hydroxycitrate; and administering the T cells to the mammal after culturing the cells in the presence of hydroxycitric acid, and/or the salt thereof.

Further embodiments of the invention provide isolated populations of T cells produced by the method, related pharmaceutical compositions, and related methods of treating or preventing cancer in a mammal.

BRIEF DESCRIPTION OF THE SEVERAL VIEWS OF THE DRAWING(S)

FIG. 1 is a schematic representation of the molecular pathways, substrates and the associated enzymes involved in the generation of mitochondrial and cytoplasmic AcCoA pools. ACLY (ATP-citrate lyase), ACSS1 (acyl-CoA synthetase short-chain family member 1), ACSS2 (acyl-CoA synthetase short-chain family member 2), CTP—citrate transporter, potassium hydroxycitrate (Hydroxycitrate-5 mM), Acetate (5 mM).

FIG. 3A is a graph showing the percentages of cells (% of maximum) expressing CD62L following treatment with negative control (a), potassium hydroxycitrate (2-HC) (b), or potassium hydroxycitrate and acetate (c).

FIG. 3B is a graph showing the mean fluorescence intensity (MFI) measured in CD62L positive cells ($\times 10^3$) following treatment with negative control (a), potassium hydroxycitrate (2-HC) (b), or potassium hydroxycitrate and acetate (c). * * * * $P<0.0001$.

FIG. 7A is a schematic of control or potassium hydroxycitrate (2-HC) T cell culture conditions.

FIGS. 7B-7C are graphs showing the quantification of CD62L positive cells (% of CD8+ cells) (FIG. 7B) and IFN-γ+ production (% of CD8+ cells) (FIG. 7C) in T cells cultured in control (a) or potassium hydroxycitrate (2-HC) (5 mM) (b). Center values and error bars represent mean±s.e.m. * * * $P<0.001$.

FIG. 15 is a schematic of control/potassium hydroxycitrate/Citrate T cell culture conditions and adoptive T cell transfer into mice bearing B16-mhgp100 tumors.

FIG. 16 is a graph showing the quantification of CD8+ 45.1+ cells ($\times 10^6$) persisting in spleen 10 days after adoptive transfer of T cells cultured in control (a), citrate (b), or potassium hydroxycitrate (2-HC) (c). Center values and error bars represent mean±s.e.m. * * P<0.01. * * P<0.01.

Figures 17A, 17B, 17C:
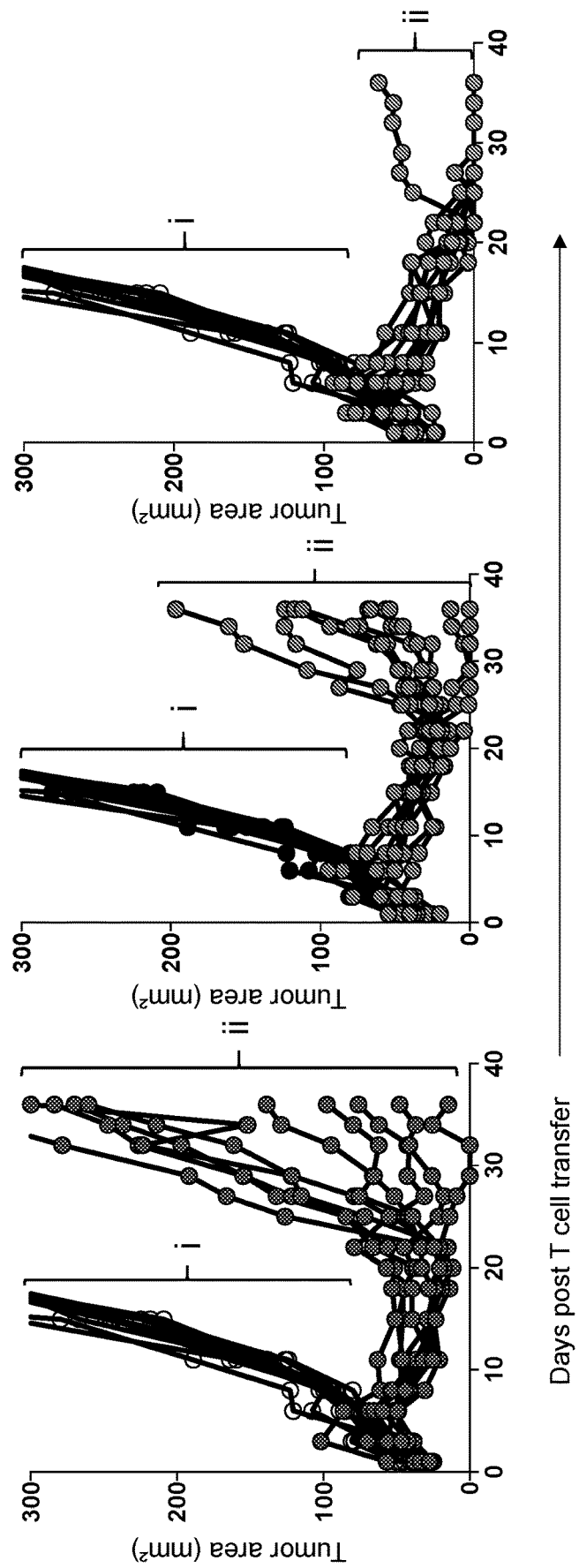

FIGS. 17A-17C are graphs showing the tumor size (mm$^2$) in mice bearing B16-mhgp100 at the indicated number of days following treatment with Pmel-1 T cells cultured in control (n=10) ((ii); FIG. 17A) or potassium hydroxycitrate (2-HC) (n=10) ((ii); FIG. 17B) or Citrate (n=10) ((ii); FIG. 17C). Untreated mice (i) served as a control.

Figure 18A:
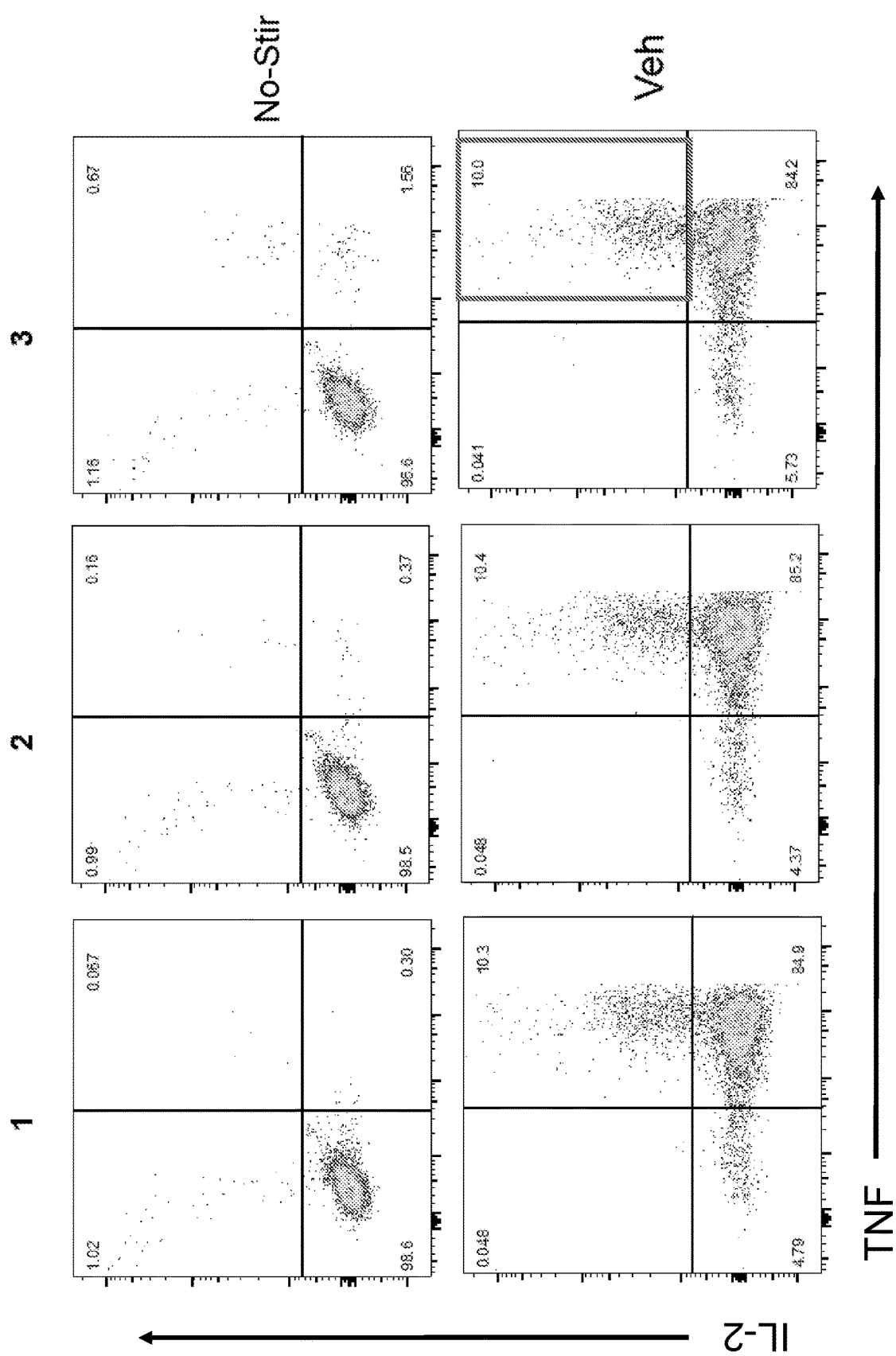
Figure 18B:
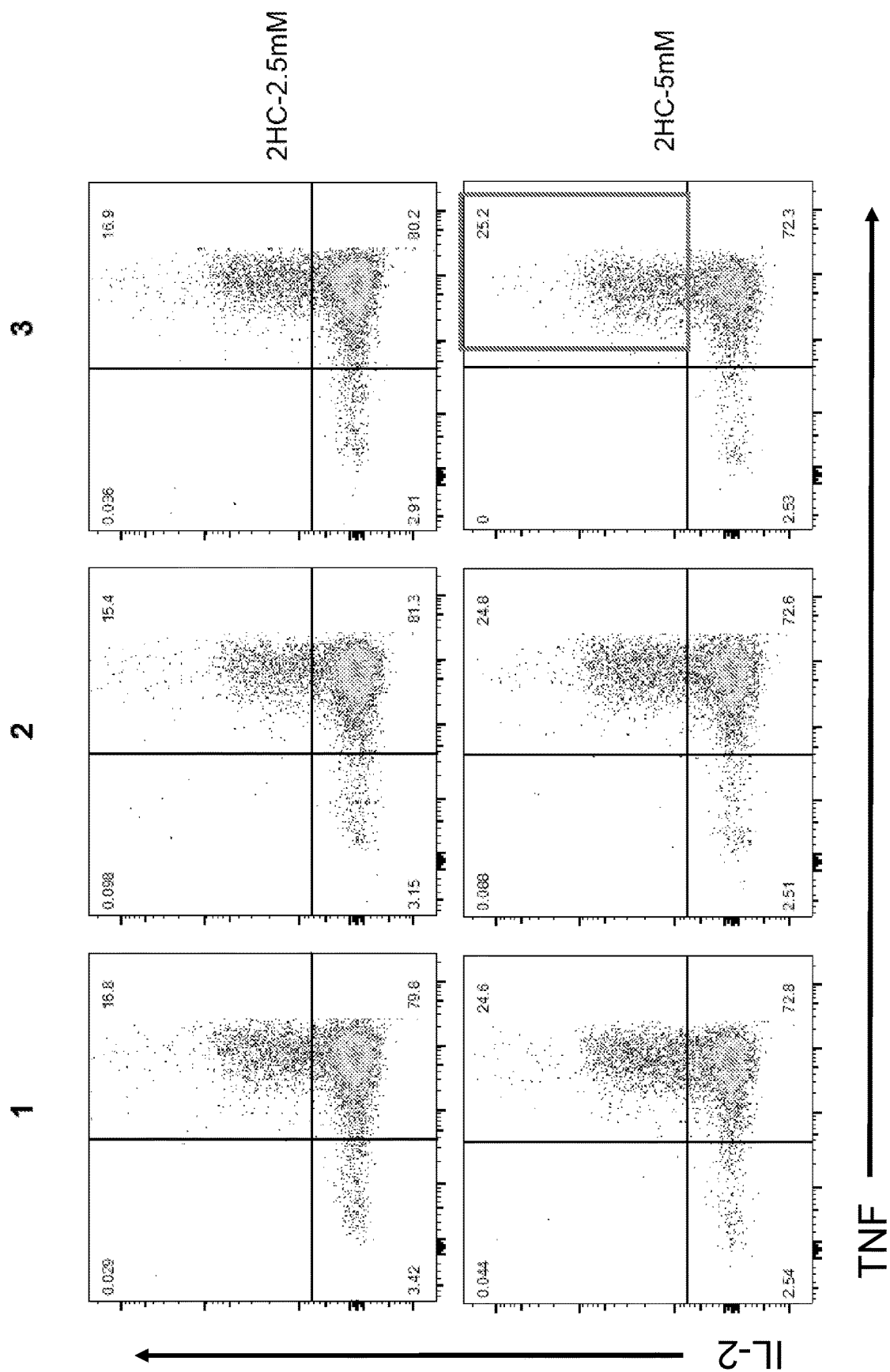

FIGS. 18A-18B present representative fluorescence-activated cell sorting (FACS) data for human TIL from Donors 1-3 cultured without stimulation (No-Stim) (FIG. 18A), in vehicle (Veh) (FIG. 18A), or in potassium hydroxycitrate (2-HC) (2.5 or 5 mM) (FIG. 18B). The cells were analyzed for the expression of tumor necrosis factor (TNF) and IL-2. The numbers in the quadrants represent the number of cells with the following phenotypes: IL-2+/TNF+ (upper right quadrant), IL-2−/TNF− (lower left quadrant), IL-2+/TNF− (upper left quadrant), and IL-2−/TNF+ (lower right quadrant).

Figure 19A:
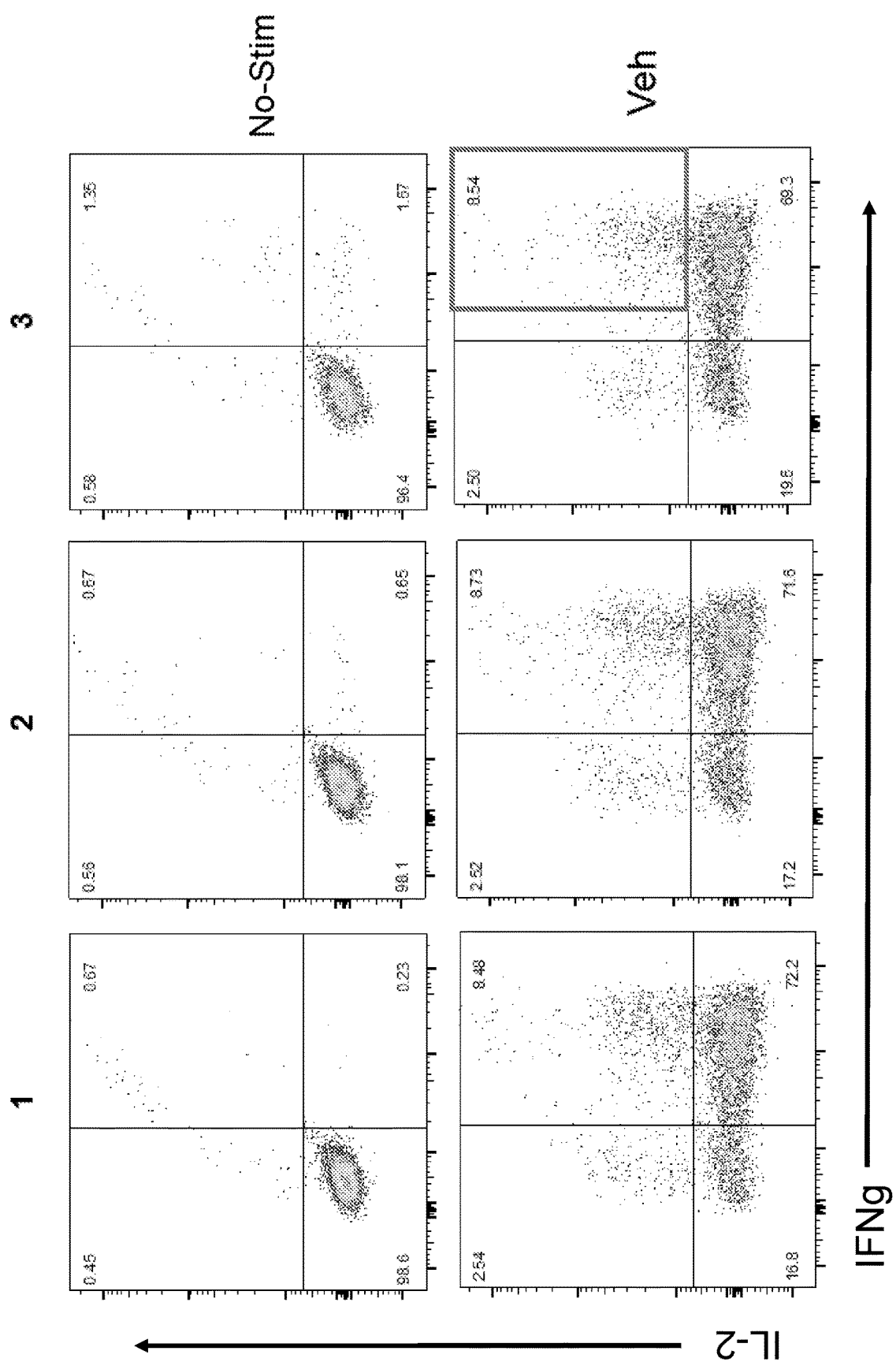
Figure 19B:
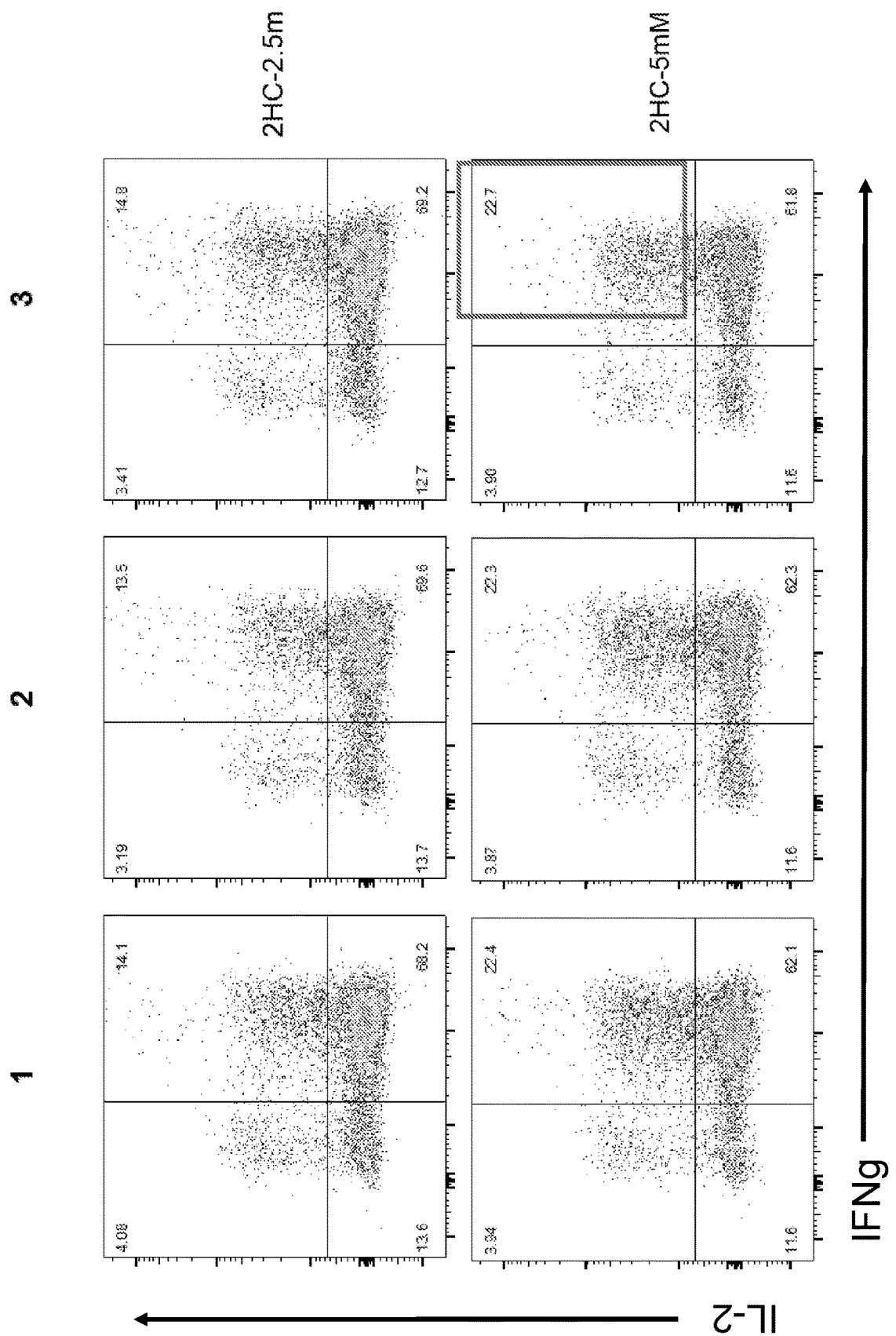

FIGS. 19A-19B present representative FACS data for human TIL from Donors 1-3 cultured without stimulation (No-Stim) (FIG. 19A), in vehicle (Veh) (FIG. 19A), or in potassium hydroxycitrate (2-HC) (2.5 or 5 mM) (FIG. 19B). The cells were analyzed for the expression of TNF and IL-2. The numbers in the quadrants represent the number of cells with the following phenotypes: IL-2+/TNF+ (upper right quadrant), IL-2−/TNF− (lower left quadrant), IL-2+/TNF− (upper left quadrant), and IL-2−/TNF+ (lower right quadrant).

Figure 20:
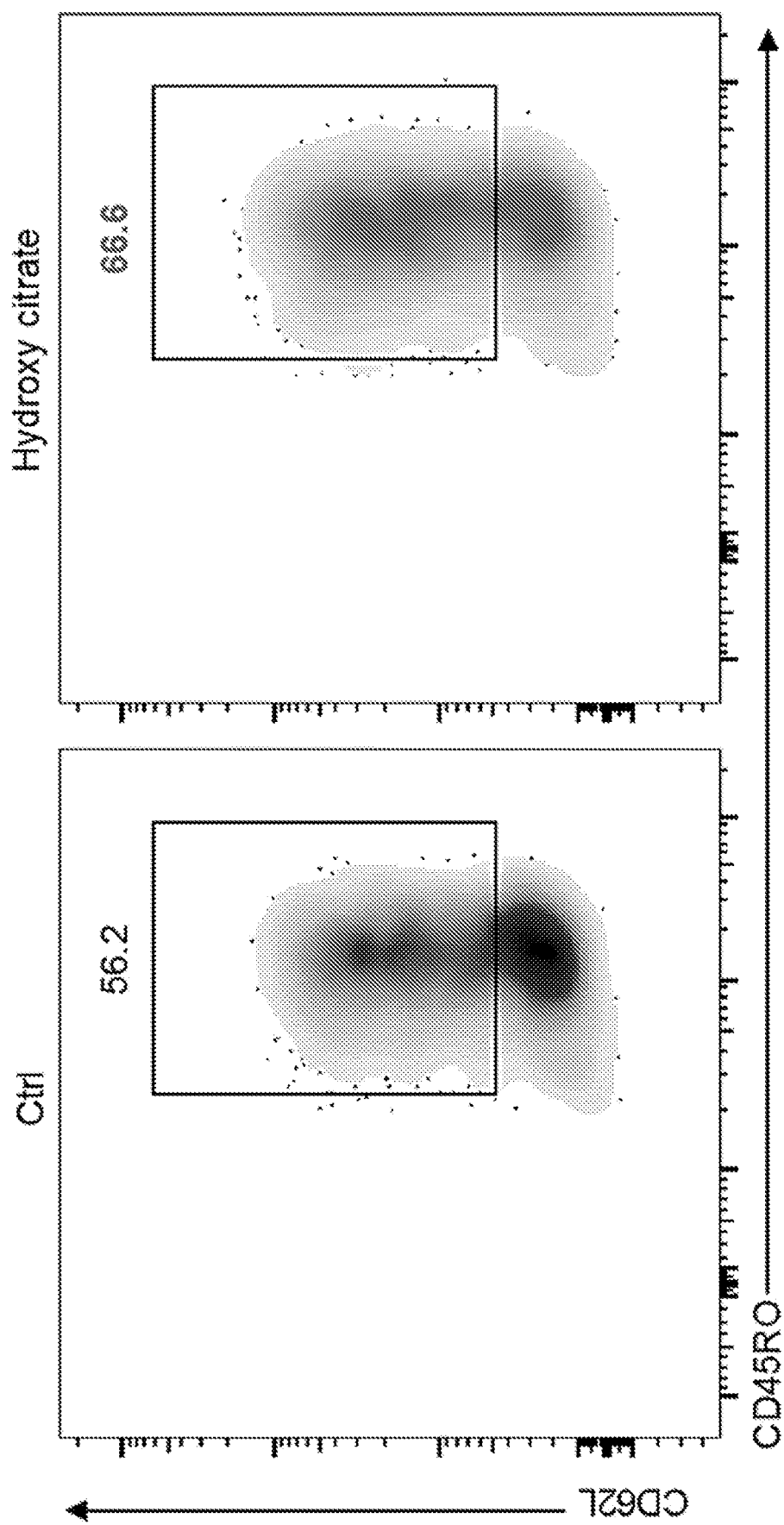

FIG. 20 presents representative FACS data for human TIL showing relatively higher expression of the lymphoid homing marker CD62L during TIL expansion for hydroxycitric acid cultured TILs as compared to control TILs.

Figure 21:
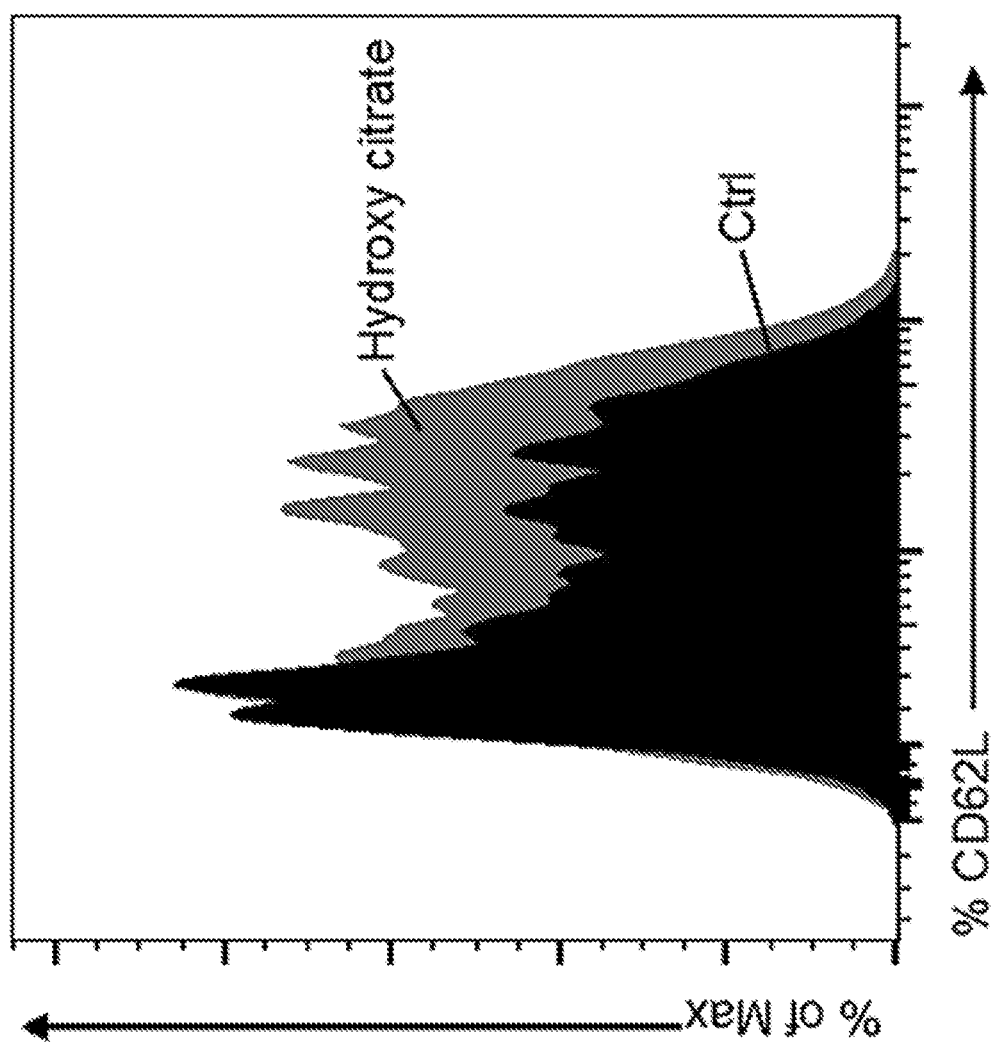

FIG. 21 is a graph showing the percentages of cells (% of maximum) expressing CD62L following treatment with negative control or potassium hydroxycitrate.

Figure 22B:
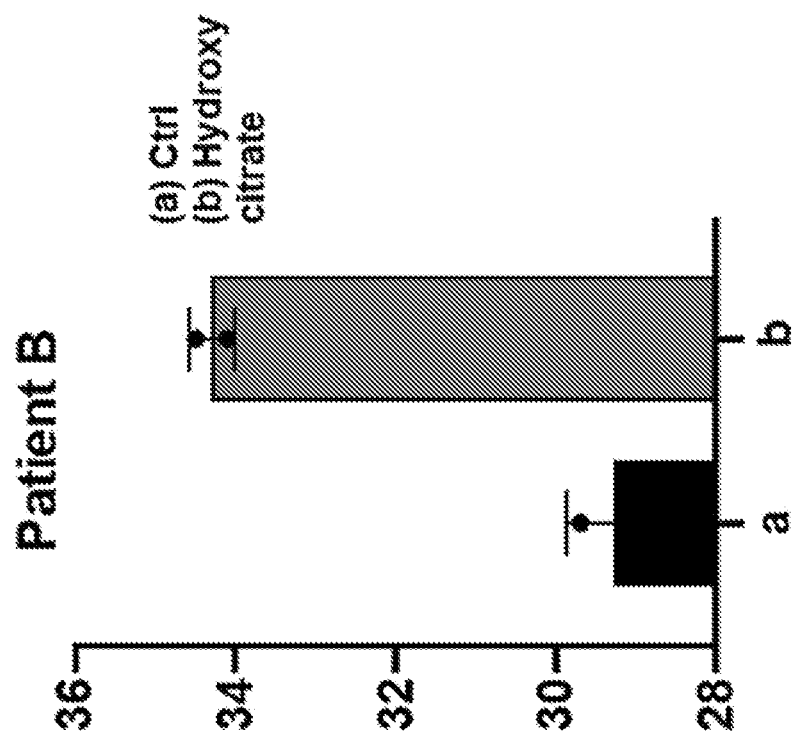
Figure 22A:
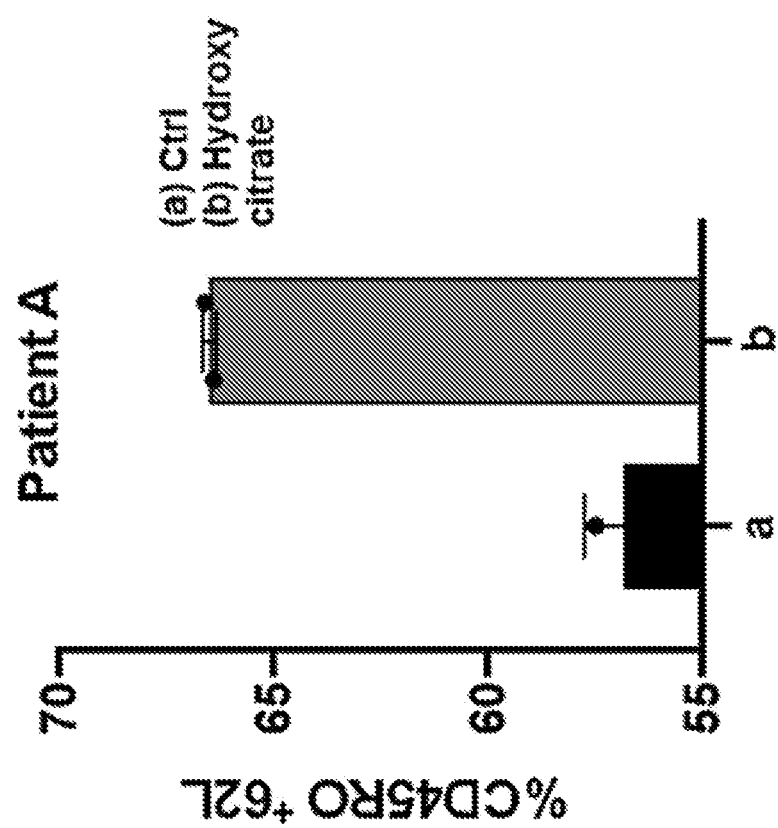

FIGS. 22A and 22B show the quantification of the data shown in FIG. 21 for CD45RO$^+$CD62L$^+$. The negative control and potassium hydroxycitrate bars are shown in FIG. 22A for Patient A and FIG. 22B for Patient B.

DETAILED DESCRIPTION OF THE INVENTION

It has been discovered that T cells which have been cultured in the presence of hydroxycitric acid, and/or a salt thereof may provide any one or more of a variety of advantages. These advantages may include, for example, any one or more of greater persistence, greater antitumor activity, decreased apoptosis, and decreased differentiation as compared to control T cells, wherein the control T cells are identical to the T cells which have been cultured in the presence of the hydroxycitric acid and/or salt thereof except that the control T cells are not cultured in the presence of the hydroxycitric acid and/or salt thereof.

An embodiment of the invention provides a method of producing an isolated population of T cells. The method may comprise culturing isolated T cells in vitro in the presence of hydroxycitric acid, and/or a salt thereof. The hydroxycitrate salt may be, for example, potassium hydroxycitrate or sodium hydroxycitrate. In a preferred embodiment, the hydroxycitrate salt is potassium hydroxycitrate. Culturing the T cells may comprise culturing the T cells in any cell culture medium comprising hydroxycitric acid and/or a salt thereof. Examples of cell culture media which may be useful in the inventive methods include those which are typically used for culturing T cells and may include, e.g., Roswell Park Memorial Institute (RPMI) 1640 medium, AIM V medium (ThermoFisher Scientific, Waltham, MA), or a combination thereof (e.g., Aim V:RPMI (50:50) medium). Such commercially available cell culture media (namely, "off the shelf" media) may lack hydroxycitric acid and hydroxycitrate salt(s). The method may comprise adding the hydroxycitric acid and/or hydroxycitrate salt(s) to the cell culture medium which lacks the hydroxycitric acid and hydroxycitrate salt(s) for use in the inventive methods. Cell culture medium which lacks hydroxycitric acid and hydroxycitrate salts is referred to herein as "control cell culture medium" or "control cell culture media."

In an embodiment of the invention, the method comprises culturing the T cells in the presence of about 1.0 mM to about 10.0 mM of hydroxycitrate salt. For example, the T cells may be cultured in the presence of about 1.0 mM, about 1.5 mM, about 2.0 mM, about 2.5 mM, about 3.0 mM, about 3.5 mM, about 4.0 mM, about 4.5 mM, about 5.0 mM, about 5.5 mM, about 6.0 mM, about 6.5 mM, about 7.0 mM, about 7.5 mM, about 8.0 mM, about 8.5 mM, about 9.0 mM, about 9.5 mM, about 10.0 mM, or any concentration bounded by any two of the above endpoints. In a preferred embodiment, the method comprises culturing the T cells in the presence of about 2.0 mM to about 6.0 mM of hydroxycitrate salt.

In an embodiment of the invention, the method comprises culturing the T cells in the presence of about 1.0 mM to about 10.0 mM of hydroxycitric acid. For example, the T cells may be cultured in the presence of about 1.0 mM, about 1.5 mM, about 2.0 mM, about 2.5 mM, about 3.0 mM, about 3.5 mM, about 4.0 mM, about 4.5 mM, about 5.0 mM, about 5.5 mM, about 6.0 mM, about 6.5 mM, about 7.0 mM, about 7.5 mM, about 8.0 mM, about 8.5 mM, about 9.0 mM, about 9.5 mM, about 10.0 mM, or any concentration bounded by any two of the above endpoints. In a preferred embodiment, the method comprises culturing the T cells in the presence of about 2.0 mM to about 6.0 mM of hydroxycitric acid.

The T cells can be cultured in the presence of hydroxycitric acid and/or a salt thereof (i.e., a sodium salt or a potassium salt). The hydroxycitric acid salt can exist as a monobasic salt, dibasic salt, or tribasic salt. For example the hydroxycitrate salt can be hydroxycitric acid monopotassium salt, hydroxycitric acid dipotassium salt, hydroxycitric acid tripotassium salt, hydroxycitric acid monosodium salt, hydroxycitric acid disodium salt, or hydroxycitric acid trisodium salt. In certain embodiments, the hydroxycitric acid salt is a hydrate thereof.

The cell culture medium may further comprise any of a variety of additives. For example, the cell culture medium may further comprise one or more antibodies and/or one or more cytokines.

The method may further comprise isolating cells from a mammal by any suitable method known in the art. For example, the cells can be obtained from the mammal by a blood draw or a leukapheresis. In an embodiment of the invention, the cells comprise peripheral blood mononuclear cells (PBMC). Preferably, the cells comprise T cells. In this regard, the method may further comprise isolating T cells from a mammal. Alternatively or additionally, the T cells can be obtained from a tumor sample taken from the mammal. In this regard, the T cells may be tumor infiltrating lymphocytes (TIL).

The population of T cells may include any type of T cells. For example, the T cells may be a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, tumor, or other tissues or fluids. T cells can also be enriched for or purified. The T cell may be a human T cell. The T cell can be any type of T cell and can be of any developmental stage, including but not limited to, $CD4^+/CD8^+$ double positive T cells, $CD4^+$ T cells, e.g., $Th_1$ and $Th_2$ cells, $CD8^+$ T cells (e.g., cytotoxic T cells), $Th_9$ cells, TIL, memory T cells, naïve T cells, and the like. The T cell may be a $CD8^+$ T cell or a $CD4^+$ T cell. In a preferred embodiment, the T cells are TIL.

Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). It is preferred that the mammals are non-human primates, e.g., of the order Primates, Ceboids, or Simoids (monkeys) or of the order Anthropoids (humans and apes). In some embodiments, the mammal may be a mammal of the order Rodentia, such as mice and hamsters. In other embodiments, the mammal is not a mouse. Preferably, the mammal is a non-human primate or a human. An especially preferred mammal is the human.

In an embodiment of the invention, the method comprises culturing the cells in the presence of (a) hydroxycitric acid and/or a salt thereof and (b) a cytokine such as, for example, interleukin-2 (IL-2), interleukin-7 (IL-7), interleukin-15 (IL-15), interleukin-12 (IL-12) or a combination of two or more of the foregoing cytokines.

In an embodiment of the invention, the T cells have antigenic specificity for a cancer antigen. The term "cancer antigen," as used herein, refers to any molecule (e.g., protein, polypeptide, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells. Cancer antigens are known in the art and include, for instance, CXorf61, mesothelin, CD19, CD22, CD276 (B7H3), gp100, MART-1, Epidermal Growth Factor Receptor Variant III (EGFRVIII), TRP-1, TRP-2, tyrosinase, NY-ESO-1 (also known as CAG-3), MAGE-1, MAGE-3, etc.

The cancer may be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, cholangiocarcinoma, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In certain preferred embodiments, the antigen-specific receptor has specificity for a melanoma antigen. In certain preferred embodiments, the antigen-specific receptor has specificity for a breast cancer antigen.

In an embodiment of the invention, the cancer antigen is a cancer neoantigen. A cancer neoantigen is an immunogenic mutated amino acid sequence which is encoded by a cancer-specific mutation. Cancer neoantigens are not expressed by normal, non-cancerous cells and may be unique to the patient. ACT with T cells which have antigenic specificity for a cancer neoantigen may provide a "personalized" therapy for the patient.

Accordingly, in an embodiment of the invention, the method may further comprise obtaining the isolated T cells by screening T cells obtained from a mammal for the T cells having antigenic specificity for the cancer neoantigen. The screening may be carried out in the presence or absence of hydroxycitric acid and/or a salt thereof. The method may further comprise isolating the T cells having antigenic specificity for the cancer neoantigen from the cells obtained from the mammal. The isolating of the T cells may be carried out in the presence or absence of hydroxycitric acid and/or a salt thereof. The T cells obtained in this manner may then be cultured in the presence of hydroxycitric acid and/or a salt thereof as described herein with respect to other aspects of the invention. Methods of screening and isolating T cells having antigenic specificity for a cancer neoantigen are described in, for example, U.S. Patent Application Publication Nos. 2017/0218042 and 2017/0224800 and Tran et al., *Science*, 344(9): 641-645 (2014).

The T cells may comprise and express an antigen-specific receptor. The phrases "antigen-specific" and "antigenic specificity," as used herein, mean that the antigen-specific receptor can specifically bind to and immunologically recognize an antigen, or an epitope thereof, such that binding of the antigen-specific receptor to antigen, or the epitope thereof, elicits an immune response. Preferably, the antigen-specific receptor has antigenic specificity for a cancer antigen (also termed a tumor antigen or a tumor-associated antigen).

In an embodiment of the invention, the antigen-specific receptor is a T-cell receptor (TCR). A TCR generally comprises two polypeptides (i.e., polypeptide chains), such as an α-chain of a TCR, a β-chain of a TCR, a γ-chain of a TCR, a δ-chain of a TCR, or a combination thereof. Such polypeptide chains of TCRs are known in the art. The antigen-specific TCR can comprise any amino acid sequence, provided that the TCR can specifically bind to and immunologically recognize an antigen, such as a cancer antigen or epitope thereof.

The T cell can comprise and express an endogenous TCR, i.e., a TCR that is endogenous or native to (naturally-occurring on) the T cell. In such a case, the T cell comprising the endogenous TCR can be a T cell that was isolated from a mammal which is known to express the particular cancer antigen. In certain embodiments, the T cell is a primary T cell isolated from a mammal afflicted with cancer. In some embodiments, the cell is a TIL or a T cell isolated from a human cancer patient.

In some embodiments, the mammal from which a cell is isolated is immunized with an antigen of, or specific for, a cancer. The mammal may be immunized prior to obtaining the cell from the mammal. In this way, the isolated cells can include T cells induced to have specificity for the cancer to be treated, or can include a higher proportion of cells specific for the cancer.

Alternatively, a T cell comprising and expressing an endogenous antigen-specific TCR can be a T cell within a mixed population of cells isolated from a mammal, and the mixed population can be exposed to the antigen which is recognized by the endogenous TCR while being cultured in vitro. In this manner, the T cell which comprises the TCR that recognizes the cancer antigen expands or proliferates in vitro, thereby increasing the number of T cells having the endogenous antigen-specific TCR.

The cell comprising an endogenous antigen-specific TCR can also be modified to express one or more nucleic acids encoding an exogenous (e.g., recombinant) antigen-specific receptor. Such exogenous antigen-specific receptors, e.g., exogenous TCRs and chimeric antigen receptors (CARs) (described in more detail below), can confer specificity for additional antigens to the T cell beyond the antigens for which the endogenous TCR is naturally specific. This can, but need not, result in the production of a T cell having dual antigen specificities.

In an embodiment of the invention, the method further comprises introducing a nucleic acid encoding an exogenous TCR into the cells under conditions to express the exogenous TCR by the cells. By "exogenous" is meant that the TCR is not native to (naturally-occurring on) the cell. The exogenous TCR may be a recombinant TCR. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the antigen-specific TCR can be a chimeric or hybrid TCR comprised of amino acid sequences derived from TCRs from two different mammalian species. For example, the exogenous antigen-specific TCR can comprise a variable region derived from a human TCR and a constant region of a mouse TCR such that the TCR is "murinized." Recombinant TCRs and methods of making them are known in the art. See, for example, U.S. Pat. Nos. 7,820,174; 7,915,036; 8,088,379; 8,216,565; 8,785,601; 9,345,748; 9,487,573; 9,879,065; 9,822,162; U.S. Patent Application Publication Nos. 2014/0378389 and 2017/0145070.

In an embodiment of the invention, the method further comprises introducing a nucleic acid encoding a CAR into the cells under conditions to express the CAR by the cells. Typically, a CAR comprises the antigen binding domain of an antibody, e.g., a single-chain variable fragment (scFv), fused to the transmembrane and intracellular domains of a TCR. Thus, the antigenic specificity of a CAR can be encoded by a scFv which specifically binds to the antigen, or an epitope thereof. CARs, and methods of making them, are known in the art. See, for example, U.S. Pat. Nos. 8,465,743; 9,266,960; 9,868,774; 9,765,342; 9,359,447; 9,790,282; and U.S. Patent Application Publication Nos. 2015/0299317 and 2016/0333422.

Any suitable nucleic acid encoding an antigen-specific receptor can be used. The antigen-specific receptor encoded by the nucleic acid can be of any suitable form including for example, a single-chain TCR, a single chain CAR, or a fusion with other proteins or polypeptides (e.g., without limitation co-stimulatory molecules). While the introducing of a nucleic acid encoding an antigen-specific receptor into the cells may be carried out in control cell culture medium, in a preferred embodiment, the introducing of a nucleic acid encoding an antigen-specific receptor into the cells is carried out in the presence of hydroxycitric acid and/or a salt thereof.

The nucleic acids may be introduced into the cell using any suitable method such as, for example, transfection, transduction, or electroporation. For example, cells can be transduced with viral vectors using viruses (e.g., retrovirus or lentivirus) and cells can be transduced with transposon vectors using electroporation.

The terms "nucleic acid" and "polynucleotide," as used herein, refer to a polymeric form of nucleotides of any length, either ribonucleotides (RNA) or deoxyribonucleotides (DNA). These terms refer to the primary structure of the molecule, and thus include double- and single-stranded DNA, double- and single-stranded RNA, and double-stranded DNA-RNA hybrids. The terms include, as equivalents, analogs of either RNA or DNA made from nucleotide analogs and modified polynucleotides such as, though not limited to, methylated and/or capped polynucleotides. In an embodiment of the invention, the nucleic acid is complementary DNA (cDNA).

The term "nucleotide" as used herein refers to a monomeric subunit of a polynucleotide that consists of a heterocyclic base, a sugar, and one or more phosphate groups. The naturally occurring bases (guanine (G), adenine (A), cytosine (C), thymine (T), and uracil (U)) are typically derivatives of purine or pyrimidine, though the invention includes the use of naturally and non-naturally occurring base analogs. The naturally occurring sugar is the pentose (five-carbon sugar) deoxyribose (which forms DNA) or ribose (which forms RNA), though the invention includes the use of naturally and non-naturally occurring sugar analogs. Nucleic acids are typically linked via phosphate bonds to form nucleic acids or polynucleotides, though many other linkages are known in the art (e.g., phosphorothioates, boranophosphates, and the like). Methods of preparing polynucleotides are within the ordinary skill in the art (Green and Sambrook, *Molecular Cloning: A Laboratory Manual*, (4th Ed.) Cold Spring Harbor Laboratory Press, New York (2012)).

The nucleic acids described herein can be incorporated into a recombinant expression vector. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors may not be naturally-occurring as a whole. However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector. Examples of recombinant expression vectors that may be useful in the inventive methods include, but are not limited to, plasmids, viral vectors (retroviral vectors, gamma-retroviral vectors, or lentiviral vectors), and transposons. The vector may then, in turn, be introduced into the cells by any suitable technique such as, e.g., gene editing, transfection, transformation, or transduction as described, for example, Green and Sambrook, *Molecular Cloning: A Laboratory Manual* (4th Ed.), Cold Spring Harbor Laboratory Press (2012). Many transfection techniques are known in the art and include, for example, calcium phosphate DNA co-precipitation; DEAE-dextran; electroporation; cationic liposome-mediated transfection; tungsten particle-facilitated microparticle bombardment; and strontium phosphate DNA co-precipitation. Phage or viral vectors can be introduced into host cells, after growth of infectious particles in suitable packaging cells, many of which are commercially available.

While the cells may be cultured in the presence of hydroxycitric acid and/or a salt thereof intermittently in vitro, in a preferred embodiment of the invention, the cells are cultured in the presence of hydroxycitric acid and/or a salt thereof for the entire duration of in vitro culture, including during expansion of the numbers of cells and during any introduction of a nucleic acid encoding an antigen-specific T-cell receptor or chimeric antigen receptor into the cells.

In an embodiment of the invention, the method further comprises expanding the number of cells in the presence of (i) hydroxycitric acid and/or a salt thereof and (ii) one or both of (a) one or more cytokines and (b) one or more non-specific T cell stimuli. Examples of non-specific T cell stimuli include, but are not limited to, one or more of irradiated allogeneic feeder cells, irradiated autologous feeder cells, anti-CD3 antibodies (e.g., OKT3 antibody), anti-4-1BB antibodies, and anti-CD28 antibodies. In preferred embodiment, the non-specific T cell stimulus may be anti-CD3 antibodies and anti-CD28 antibodies conjugated to beads. Any one or more cytokines may be used in the inventive methods. Exemplary cytokines that may be useful for expanding the numbers of cells include interleukin (IL)-2, IL-7, IL-21, and IL-15.

Expansion of the numbers of cells can be accomplished by any of a number of methods as are known in the art as described in, for example, U.S. Pat. Nos. 8,034,334; 8,383, 099; and U.S. Patent Application Publication No. 2012/ 0244133. In an embodiment of the invention, the numbers of cells are expanded by physically contacting the cells with one or more non-specific T cell stimuli and one or more cytokines in the presence of hydroxycitric acid and/or a salt thereof. For example, expansion of the numbers of cells may be carried out by culturing the cells with OKT3 antibody, IL-2, and feeder PBMC (e.g., irradiated allogeneic PBMC) in the presence of hydroxycitric acid, and/or a salt thereof. In an embodiment of the invention, expanding the number of cells in the presence of hydroxycitric acid and/or a salt thereof comprises culturing the cells for at least about 14 days in the presence of hydroxycitric acid and/or a salt thereof.

In an embodiment of the invention, the method comprises nonspecifically stimulating the T cells in the presence of hydroxycitric acid and/or a salt thereof. Nonspecific stimulation may be carried out by contacting the T cells with any one or more of the non-specific T cell stimuli described herein with respect to other aspects of the invention.

In an embodiment of the invention, the method comprises specifically stimulating the T cells in the presence of hydroxycitric acid, and/or a salt thereof. Specific stimulation may be carried out by contacting the T cells with the cancer antigen for which the T cells have antigenic specificity. For example, the T cells may be co-cultured with antigen presenting cells (APCs) which express the cancer antigen, e.g., (i) APCs which have been pulsed with the cancer antigen or (ii) APCs into which a nucleotide sequence encoding the cancer antigen has been introduced.

An embodiment of the invention further provides an isolated or purified population of T cells produced by any of the inventive methods described herein. The populations of T cells produced by the inventive methods may provide many advantages. For example, administering T cells cultured in the presence of hydroxycitric acid and/or a salt thereof to a mammal may provide any one or more of greater persistence, greater antitumor activity, decreased apoptosis, and decreased differentiation as compared to administering control cells, wherein the control cells are identical to the cells cultured in the presence of hydroxycitric acid and/or a salt thereof except that the control cells are not cultured in the presence of hydroxycitric acid and/or a salt thereof.

In an embodiment of the invention, culturing T cells in the presence of hydroxycitric acid and/or a salt thereof increases expression of one or more of CD62L, IL-2, and tumor necrosis factor (TNF) by the T cells as compared to control cells, wherein the control cells are identical to the cells cultured in the presence of hydroxycitric acid and/or a salt thereof except that the control cells are not cultured in the presence of hydroxycitric acid and/or a salt thereof.

In an embodiment of the invention, cells which have been cultured in the presence of hydroxycitric acid and/or a salt thereof may be less differentiated as compared to control cells, wherein the control cells are identical to the cells cultured in the presence of hydroxycitric acid and/or a salt thereof except that the control cells are not cultured in the presence of hydroxycitric acid and/or a salt thereof. The less differentiated populations of hydroxycitric acid, and/or a salt thereof-cultured T cells produced according to the inventive methods may, advantageously, reduce or avoid the production of T cells with a terminally differentiated phenotype that is associated with diminished antitumor activity and poor capacity for long-term persistence in vivo.

In an embodiment of the invention, the hydroxycitric acid and/or a salt thereof—cultured T cells have a naïve T cell ($T_N$), T memory stem cell ($T_{SCM}$), or central memory T cell ($T_{CM}$) phenotype. Alternatively or additionally, the hydroxycitric acid, and/or a salt thereof-cultured T cells lack an effector memory T cell ($T_{EM}$) phenotype. For example, CCR7 and CD62L are expressed by $T_N$, $T_{SCM}$, and $T_{CM}$ cells, but are not expressed by $T_{EM}$ cells. The transcription factors LEF1, FOXP1, and KLF7 are expressed by $T_N$, $T_{SCM}$, and $T_{CM}$ cells, but are not expressed by $T_{EM}$ cells. CD45RO and KLRG1 are not expressed by $T_N$ or $T_{SCM}$ cells, but are expressed by $T_{EM}$ cells. Gattinoni et al., *Nat. Rev. Cancer*, 12: 671-84 (2012). In an embodiment of the invention, T cells cultured in the presence of the hydroxycitric acid and/or a salt thereof may be any one or more of $CD62L^+$, $KLRG1^-$, $LEF1^+$, $FOXP1^+$, and $KLF7^+$, $CCR7^+$, $CD57^+$, and $CD45RO^-$. The T cells may be $CD62L^+$. Alternatively or additionally, the T cells may be $CD8^+$. In an especially preferred embodiment, the T cells cultured in the presence of hydroxycitric acid and/or a salt thereof may be less differentiated T cells that are both $CD62L^+$ and $CD8^+$.

In an embodiment of the invention, the T cells produced according to the inventive methods have an increased expression of genes associated with a $T_N$, $T_{SCM}$, or $T_{CM}$ phenotype. For example, T cells cultured in the presence of hydroxycitric acid and/or a salt thereof according to the inventive methods may have a higher expression of CD27 and/or CD28 as compared to control T cells, wherein the control T cells are identical to the T cells cultured in the presence of hydroxycitric acid and/or a salt thereof except that the control T cells are not cultured in the presence of hydroxycitric acid and/or a salt thereof. Without being bound to a particular theory or mechanism, it is believed that CD27 and CD28 are associated with proliferation, in vivo persistence, and a less differentiated state of T cells (the increased differentiation of T cells is believed to negatively affect the capacity of T cells to function in vivo). T cells expressing higher levels of CD27 are believed to have better antitumor activity than CD27-low cells.

The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70% or about 80%, about 90% or can be about 100%.

The population of cells produced by culturing cells in the presence of hydroxycitric acid and/or a salt thereof according to the inventive methods can be a heterogeneous population comprising the cells described herein, in addition to at least one other cell, e.g., a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells produced by the inventive methods can be a substantially homogeneous population, in which the population comprises mainly of the cells, e.g., T cells described herein. The population also can be a clonal population of cells, in which all cells of the population are clones of a single cell, e.g., T cell. In one embodiment of the invention, the population of cells is a clonal population comprising cells, e.g., T cells comprising a recombinant expression vector encoding the antigen-specific receptor as described herein.

The inventive isolated or purified population of cells produced according to the inventive methods may be included in a composition, such as a pharmaceutical composition. In this regard, an embodiment of the invention provides a pharmaceutical composition comprising the isolated or purified population of cells described herein and a pharmaceutically acceptable carrier.

Preferably, the carrier is a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular method used to administer the population of cells. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the population of cells, and in certain instances, a particular route can provide a more immediate and more effective response than another route.

Preferably, the population of cells is administered by injection, e.g., intravenously. A suitable pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

An embodiment of the invention provides a method of administering T cells to a mammal, the method comprising culturing isolated T cells in vitro in the presence of hydroxycitric acid and/or a salt thereof, wherein the salt is potassium hydroxycitrate or sodium hydroxycitrate; and administering the T cells to the mammal after culturing the cells in the presence of hydroxycitric acid and/or a salt thereof. The culturing of the T cells in the presence of hydroxycitric acid and/or a salt thereof may be carried out as described herein with respect to other aspects of the invention. The isolated population of cells can be cultured ex vivo in the presence of hydroxycitric acid and/or a salt thereof, and then directly transferred into a mammal (preferably a human) affected by cancer. Such a cell transfer method is referred to in the art as "adoptive cell transfer" or "adoptive cell therapy" (ACT). In an embodiment of the invention, hydroxycitric acid and/or a salt thereof is removed (e.g., washed) from the cells prior to administering the cells to a mammal. In another embodiment of the invention, hydroxycitric acid and/or a salt thereof is not removed from the cells prior to administering the cells to a mammal. In an embodiment of the invention, the method comprises administering a pharmaceutical composition comprising the T cells to the mammal, wherein the pharmaceutical composition is as described herein with respect to other aspects of the invention.

The T cells administered to the mammal can be allogeneic or autologous to the mammal. In "autologous" administration methods, cells are removed from a mammal, stored (and optionally modified), and returned back to the same mammal. In "allogeneic" administration methods, a mammal receives cells from a genetically similar, but not identical, donor. Preferably, the T cells are autologous to the mammal. Autologous cells may, advantageously, reduce or avoid the undesirable immune response that may target an allogeneic cell such as, for example, graft-versus-host disease.

In the instance that the T cell(s) are autologous to the mammal, the mammal can be immunologically naïve, immunized, diseased, or in another condition prior to isolation of the cell(s) from the mammal. In some instances, it is preferable for the method to comprise immunizing the mammal with an antigen of the cancer prior to isolating the T cell(s) from the mammal, introducing nucleic acid into the cell(s), and the administering of the T cell(s) or composition thereof. As discussed herein, immunization of the mammal with the antigen of the cancer will allow a population of T cells having an endogenous TCR reactive with the cancer antigen to increase in numbers, which will increase the likelihood that a T cell obtained for culturing in the presence of hydroxycitric acid and/or a salt thereof will have a desired antigen-specific TCR.

In accordance with an embodiment of the invention, a mammal with cancer can be therapeutically immunized with an antigen from, or associated with, that cancer, including immunization via a vaccine. While not desiring to be bound by any particular theory or mechanism, the vaccine or immunogen is provided to enhance the mammal's immune response to the cancer antigen present in the cancerous tissue. Such a therapeutic immunization includes, but is not limited to, the use of recombinant or natural cancer proteins, peptides, or analogs thereof, or modified cancer peptides, or analogs thereof that can be used as a vaccine therapeutically as part of adoptive immunotherapy. The vaccine or immunogen, can be a cell, cell lysate (e.g., from cells transfected with a recombinant expression vector), a recombinant expression vector, or antigenic protein or polypeptide. Alternatively, the vaccine, or immunogen, can be a partially or substantially purified recombinant cancer protein, polypeptide, peptide or analog thereof, or modified proteins, polypeptides, peptides or analogs thereof. The protein, polypeptide, or peptide may be conjugated with lipoprotein or administered in liposomal form or with adjuvant. Preferably, the vaccine comprises one or more of (i) the cancer antigen for which the antigen-specific receptor has antigenic specificity, (ii) an epitope of the antigen, and (iii) a vector encoding the antigen or the epitope.

For purposes of the invention, the dose, e.g., number of cells administered should be sufficient to effect, e.g., a therapeutic or prophylactic response, in the mammal over a reasonable time frame. For example, the number of cells administered should be sufficient to bind to a cancer antigen or treat or prevent cancer in a period of from about 2 hours or longer, e.g., 12 to 24 or more hours, from the time of administration. In certain embodiments, the time period could be even longer. The number of cells administered will be determined by, e.g., the efficacy of the particular population of cells to be administered and the condition of the animal (e.g., human), as well as the body weight of the animal (e.g., human) to be treated.

Many assays for determining an administered number of cells are known in the art. For purposes of the invention, an assay, which comprises comparing the extent to which target cells are lysed or one or more cytokines such as, e.g., IFN-γ and IL-2 is secreted upon administration of a given number of such cells to a mammal among a set of mammals of which is each given a different number of the cells, e.g., T cells, could be used to determine a starting number to be administered to a mammal. The extent to which target cells are lysed or cytokines such as, e.g., IFN-γ and IL-2 are secreted upon administration of a certain number can be assayed by methods known in the art. Secretion of cytokines such as, e.g., IL-2, may also provide an indication of the quality (e.g., phenotype and/or effectiveness) of a T cell preparation.

The number of cells administered also will be determined by the existence, nature and extent of any adverse side effects that might accompany the administration of a particular population of cells. Typically, the attending physician will decide the number of cells with which to treat each individual patient, taking into consideration a variety of factors, such as age, body weight, general health, diet, sex, route of administration, and the severity of the condition being treated. By way of example and not intending to limit the invention, the number of cells, e.g., T cells, to be administered can be about $10 \times 10^6$ to about $10 \times 10^{11}$ cells per infusion, about $10 \times 10^9$ cells to about $10 \times 10^{11}$ cells per infusion, or $10 \times 10^7$ to about $10 \times 10^9$ cells per infusion.

It is contemplated that the populations of T cells produced by culturing the T cells in the presence of hydroxycitric acid and/or a salt thereof can be used in methods of treating or preventing cancer in a mammal. In this regard, an embodiment of the invention provides a method of treating or preventing cancer in a mammal, comprising (i) administering cells to the mammal according to any of the methods described herein; (ii) administering to the mammal the cells produced according to any of the methods described herein; or (iii) administering to the mammal any of the isolated populations of cells or pharmaceutical compositions described herein; in an amount effective to treat or prevent cancer in the mammal.

In an embodiment of the invention, the method of treating or preventing cancer may comprise administering the cells or pharmaceutical composition to the mammal in an amount effective to reduce metastases in the mammal. For example, the inventive methods may reduce metastatic nodules in the mammal.

One or more additional therapeutic agents can be coadministered to the mammal. By "coadministering" is meant administering one or more additional therapeutic agents and the isolated population of cells sufficiently close in time such that the isolated population of cells can enhance the effect of one or more additional therapeutic agents, or vice versa. In this regard, the isolated population of cells can be administered first and the one or more additional therapeutic agents can be administered second, or vice versa. Alternatively, the isolated population of cells and the one or more additional therapeutic agents can be administered simultaneously. Additional therapeutic agents that may enhance the function of the isolated population of cells may include, for example, one or more cytokines or one or more antibodies (e.g., antibodies that inhibit PD-1 function). An exemplary therapeutic agent that can be co-administered with the isolated population of cells is IL-2. Without being bound to a particular theory or mechanism, it is believed that IL-2 may enhance the therapeutic effect of the isolated population of cells, e.g., T cells.

An embodiment of the invention further comprises lymphodepleting the mammal prior to administering the isolated population of cells. Examples of lymphodepletion include, but may not be limited to, nonmyeloablative lymphodepleting chemotherapy, myeloablative lymphodepleting chemotherapy, total body irradiation, etc.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset or recurrence of the disease, or a symptom or condition thereof.

With respect to the inventive methods, the cancer can be any cancer, including any of the cancers described herein with respect to other aspects of the invention.

The following examples further illustrate the invention but, of course, should not be construed as in any way limiting its scope.

EXAMPLES

The following materials and methods were employed in the experiments described in Examples 1-9.
Study Approval.

Animal experiments were conducted with the approval of the National Cancer Institute (NCI) and National Institute of Arthritis and Musculoskeletal and Skin Diseases (NIAMS) Animal Use and Care Committees.
In Vitro Activation of T Cells.

CD8$^+$ T cells from Pmel-1 mice were stimulated in vitro with 1 μM hgp100$_{25-33}$ peptide for 5 days and secondary restimulation was done with plate-bound anti-CD3 (1 μg/ml; BD Biosciences, Franklin Lakes, NJ) and soluble anti-CD28 (1 μg/ml; BD Biosciences) and expanded in culture medium containing 60 IU of IL-2. The conditions control/potassium hydroxycitrate (FIG. 7) were activated in the above conditions for a total of 10 days. For measuring T cell effector function, these cells were stimulated on day 10 in the indicated conditions for 5 h with anti-CD3 and -CD28 without IL-2 in the presence of brefeldin A and monesin (BD Biosciences).
Mice and Cell Lines.

C57BL/6 mice (obtained from Charles River, Frederick, MD) of 6-8 weeks of age were used as recipient hosts for adoptive transfer unless otherwise indicated. Pmel-1 Ly5.1 transgenic mice were used for adoptive cell transfer. To obtain Pmel-1 Ly5.1 mice, Pmel-1(B6.Cg–/Cy Tg [TcraTcrb] 8Rest/J) mice were crossed with Ly5.1 mice (B6.SJL-PtprcaPepcb/BoyJ). All mice were maintained under specific pathogen-free conditions. Modified B16-mhgp100 (H-2D$_b$), a mouse melanoma cell line, transduced as previously described to express glycoprotein 100 (gp100) with human residues at positions 25-27; EGS to KVP residues was used as the tumor model. Cell lines were maintained in complete media DMEM (Gibco, Waltham, MA) with 10% FBS, 1% glutamine and 1% penicillin-streptomycin.
Intracellular Cytokine Staining, Phosphoflow and Flow Cytometry.

For all flow cytometry experiments, T cells were stained with a fixable live/dead stain (Invitrogen, Waltham, MA) in phosphate buffered saline (PBS) followed by surface antibody staining in FACS buffer (PBS with 0.5% bovine serum albumin (BSA) and 0.1% sodium azide). For intracellular cytokine staining, cells were first stained for surface markers and later stained for intracellular molecules following fixation and permeabilization (BD CYTOFIX/CYTOPERM fixation/permeabilization solution kit). For phospho-staining, BD PHOSFLOW reagents (BD Biosciences) were used and protocols were carried out according to the manufacturer's protocols. After washing, cells were stained with phospho-antibodies purchased from Cell Signaling (Danvers, MA). Antibodies for surface staining and intracellular cytokine staining were purchased from BD Biosciences and e Biosciences (San Diego, CA). All experiments were conducted on a BD FORTESSA flow cytometer (Becton Dickinson, Downers Grove, IL) and analyzed with FLOWJO software (TreeStar, Ashland, OR).
Adoptive Cell Transfer (ACT) and Tumor Immunotherapy.

For immunotherapy studies, C57BL/6 mice were implanted with subcutaneous melanoma line B16-mhgp100 ($5 \times 10^5$ cells). 10 days after tumor implantation, mice (n=10 for all groups) were sub-lethally irradiated (600 cGy), randomized, and injected intravenously with $5 \times 10^5$ Pmel-1 Ly5.1 T-cells transduced with control/potassium hydroxycitrate. Post T-cell transfer, mice received intraperitoneal injections of IL-2 in PBS ($18 \times 10^4$ IU per 0.5 ml) once daily for 3 days starting on the day of cell transfer. T-cell transfers and measurement of tumors were coded and performed in a blinded manner. Tumors were measured every two-three days after transfer and tumor area was calculated by length× width of the tumor. Mice with tumors approaching greater than 400 mm$^2$ were euthanized. Tumor measurements were presented as mean±s.e.m at the indicated times after ACT. Following transfer, mice were vaccinated with vaccinia rhgp100 $1 \times 10^7$ plaque-forming units (PFU). Mouse blood was obtained via sub-mandibular venipuncture at the indicated time points for CD62L phenotype and for quantification of absolute numbers.
Experimental Metastasis To understand the efficacy of adoptively transferred T cells to cure established lung tumor nodules or prevent further colonization, B16-F10 melanoma cells recombinantly expressing-mhgp100 were used. B16-F10-mhgp100 ($2 \times 10^5$) were intravenously injected into sub-lethally irradiated (600 cGy) mice. Mice were randomized and injected intravenously with $1 \times 10^5$ Pmel-1 Ly5.1 T-cells treated in control (n=10) or potassium hydroxycitrate (n=10) conditions on day 10. Two weeks later, mice were euthanized and lungs were collected to enumerate the lung nodules.
Retroviral Transduction.

Platinum-E ecotropic (PlatE) packaging cells (Cell Biolabs, San Diego, CA) were plated in complete media one day before transfections on poly-d-lysine-coated 10-cm plates (Corning, Corning, NY) at a concentration of $6 \times 10^6$ cells per plate. On the day of transfection, complete media was replaced with media without antibiotics. Packaging cells were transfected with 20 μg of retroviral plasmid DNA encoding MSGV-LC3-mcherry-eGFP-Thy1.1, MSGV-LC3G120A-mcherry-eGFP-Thy1.1 (G120A-autophagy inefficient construct) along with 12 μg pCL-Eco plasmid using 60 µl LIPOFECTAMINE 2000 transfection reagent in OPTIMEM reduced serum media (Invitrogen) for 8 hours. Medium was replaced 8 h after transfection and cells were incubated for a further 48 h in complete media. To capture the viral particles for efficient transduction, retroviral supernatants were spun at 2,000 g for 2 h at 32° C. in 24-well RETRONECTIN reagent (Takara Bio, Shiga, Japan) coated non-tissue-culture-treated plates.

AcCoA and Citrate Quantification.

T cells (n=3) cultured in control or potassium hydroxycitrate conditions were collected and washed in PBS to perform the total and cytoplasmic AcCoA and citrate levels. Samples were homogenized in 1% TRITON X-100 nonionic surfactant, 20 mM Tris-HCl, pH=7.4, 150 mM NaCl on ice for 10 min (Sigma Acetyl-Coenzyme A Assay Kit—MAK039) or citrate buffer (Sigma Citrate Assay Kit—MAK057) (Sigma, St. Louis, MO) as per the directions provided in the kit. For total AcCoA quantification, pelleted cells were extracted using 80% methanol or 5% sulfosalicylic acid with 50 µM DTT. After cell lysis, samples were deproteinized with a 10 kDa molecular weight cut-off (MWCO) spin filter prior to the assay. AcCoA concentrations were interpolated with AcCoA standards using fluorometric assay (Ex=535, Em=587) or by mass spectrometry. Citrate concentrations were interpolated with citrate standards using colorimetric assay (570 nm).

ChIP-Seq and ChIP-PCR.

Chromatin Immunoprecipitations were performed with validated antibodies from previous literatures (Gray et al., Immunity, 46(4): 596-608 (2017); Peng et al., Science, 354(6311): 481-484 (2016)) and protocols were followed according to manufacturing instructions provided by the CHIP-IT express shearing kit (Active Motif, Carlsbad, CA). Briefly, CD8+ Pmel-1 cells were fixed with formaldehyde for 7 minutes on a rocking platform and quenched with 1× of Glycine. Cells were pelleted with phenylmethylsulfonyl fluoride (PMSF) and protein inhibition cocktail and stored at −80 prior to cell lysis. Thawed cells were suspended in ice cold lysis buffer to obtain nuclei material. Nuclei material was sheared by incubating with enzymatic cocktail for 15 minutes at 37° C. Sheared chromatin with a total of 7.5 µg/sample was incubated with protein G magnetic beads with anti-H3K27Ac (Abcam Cat #ab4729), H3k9Ac (Abcam Cat #ab4441) (Abcam, Cambridge, UK) and anti IgG at 4° C. overnight. Magnetic beads were washed with buffers to remove unbound immune complexes and eluted with 150 µl of elution buffer. Obtained DNA was reverse crosslinked and purified by phenol chloroform. Concentration of the ChIP DNA was measured with high sensitive DNA assay protocol on tape station to normalize the DNA. Samples were sequenced on illumina Next seq system (Illumina, San Diego, CA) with 75 bp reads in single end mode with approximately 40M reads per sample. To validate the Chip sequencing results, ChIP-PCR was performed on Ifng locus. Chip enrichment and efficiency in different treatment conditions at the Ifng locus were performed by qPCR using the ABI SYBR Green PCR master mix amplification kit (Thermo Fischer Scientific, Waltham, MA). Chromatin enrichment for different treatment conditions was extrapolated with the standard curve produced from diluting the input DNA. The following primers were used for qPCR: Ifng promoter F:5'-GGAGCCTTCGATCAGGTATAAA-3' (SEQ ID NO: 1) Ifng promoter R: 5'-CTCAAGTCAGAGGGTCCAAAG-3' (SEQ ID NO: 2).

ChIP-Seq and Peak Calling Analysis.

Sequenced reads with single end 75 bp were obtained by using the Illumina pipeline software (Illumina). Sequenced reads were trimmed for adapters and aligned to the mouse genome (NCBI37/mm9) with Bowtie v2 and only uniquely mapped reads were retained. The output of Bowtie was converted to BAM files, which represent the genomic coordinates of each read. Bam files were normalized using RPKM and converted to coverage tracks in big wig format using deeptools (Command #BamCoverage -b Bam File --normalizeUsingRPKM --binSize 10 --smoothLength 30 -bl mm9.blacklist.bed --centerReads --minMappingQuality 30 -o Output_File.bw). Tracks generated were viewed using the IGV (Integrative Genomics Viewer). Peaks were called using Homer software with (#findPeaks Tag directory -i Input -region -size 1000 -minDist 2500 >Output.txt) and the statistical significance for enrichment between control and test conditions were calculated on 2 biological replicates with Deseq2. Volcano plots were plotted with Log fold change vs P-values obtained from Desq2 output files.

Statistical Analysis.

For adoptive transfer experiments, recipient mice were randomized before cell transfer. Tumor measurements were plotted as the mean±s.e.m. for each data point, and tumor treatment graphs were compared by using the Wilcoxon rank sum test and analysis of animal survival was assessed using a log-rank test. In all cases, P values of less than 0.05 were considered significant. Statistics were calculated using GraphPad Prism 7 software (GraphPad Software Inc., La Jolla, CA).

Example 1

This example demonstrates that potassium hydroxycitrate exposure results in citrate accumulation and depletion of cytoplasmic AcCoA in T cells.

Figure 1:
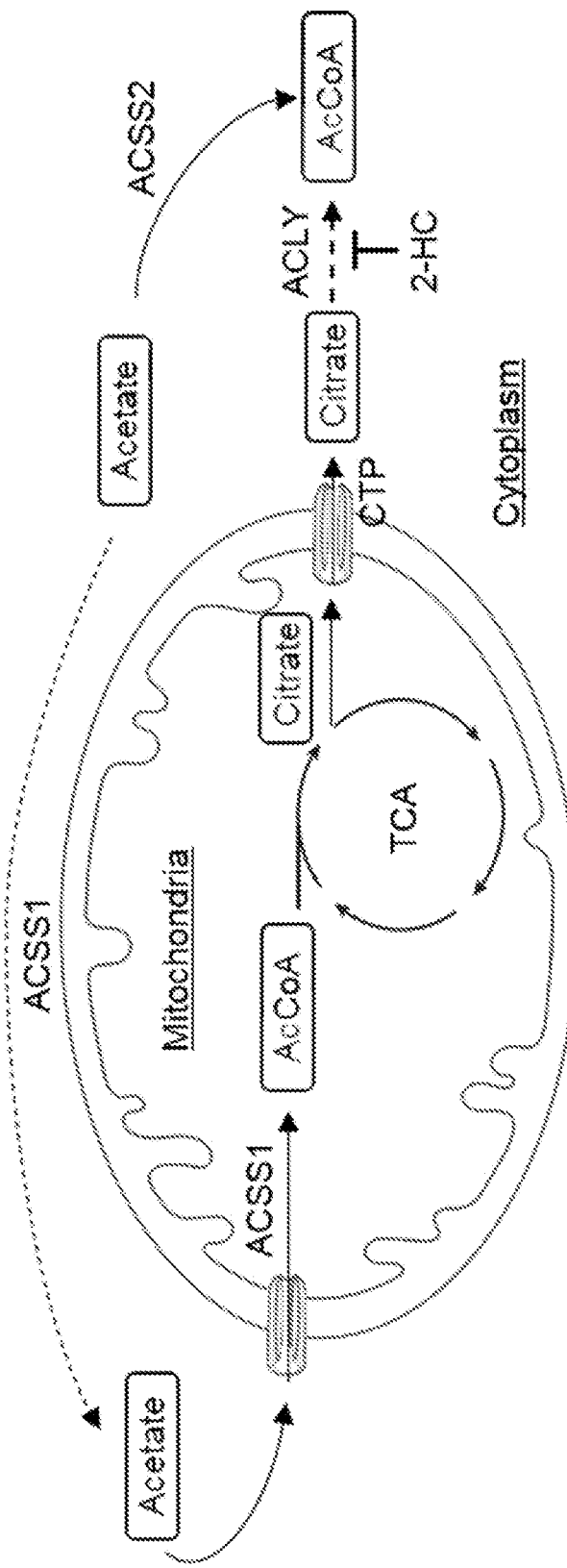

To evaluate the impact of cytoplasmic acetyl-CoA (AcCoA) abundance on T cell phenotype, manipulation of AcCoA metabolism and relative abundance was employed. Cytoplasmic AcCoA can be generated by the conversion of citrate to AcCoA and oxaloacetate by the enzyme adenosine triphosphate (ATP) citrate lyase (ACLY). The effect of 2-hydroxycitrate (potassium hydroxycitrate), an inhibitor of ACLY, on T cell maturation and function was tested (FIG. 1).

Figures 2A, 2B, 2C:
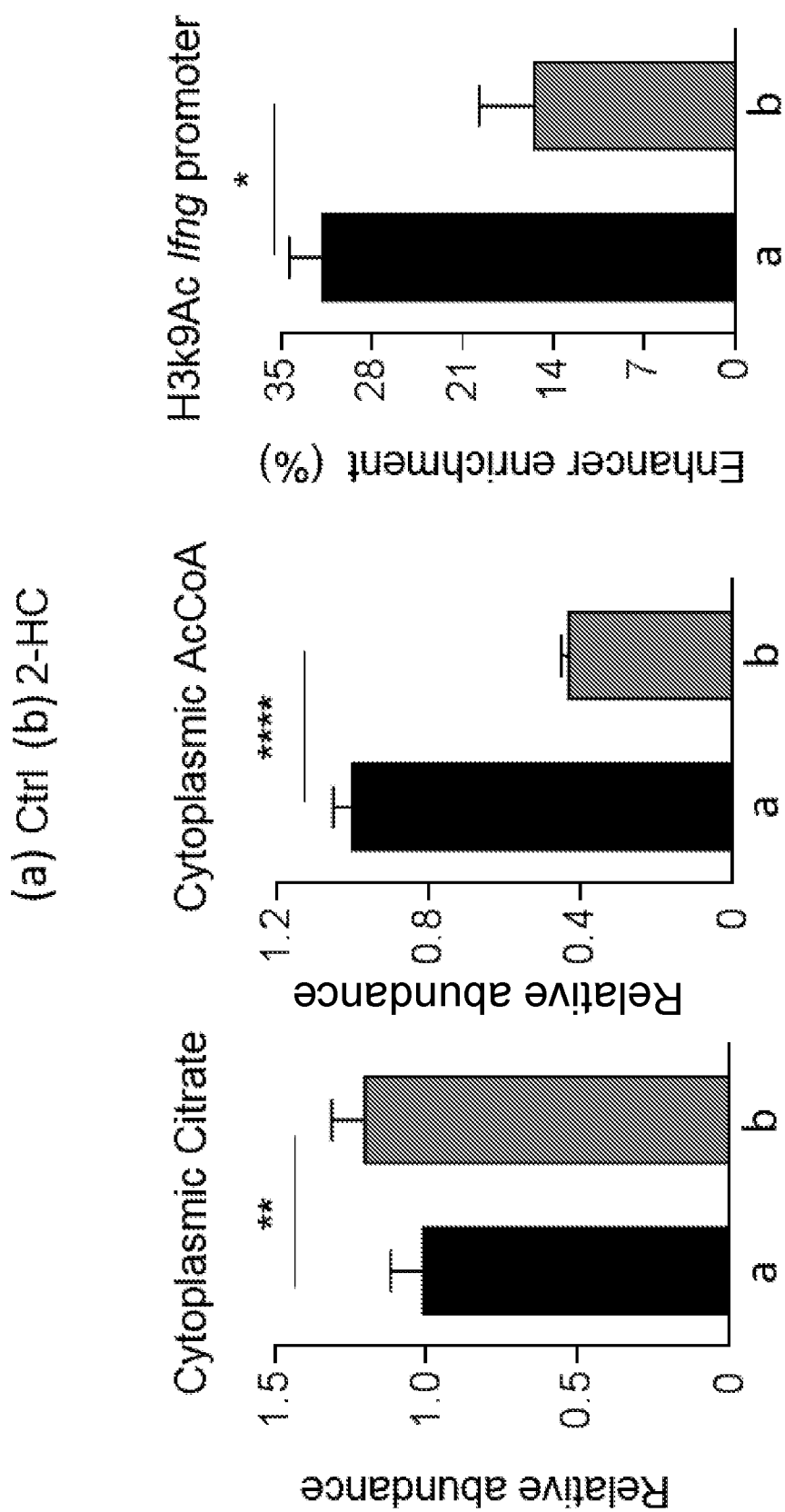
FIGS. 2A and 2B are graphs showing the quantification (relative abundance) of cytoplasmic citrate (FIG. 2A) and cytoplasmic AcCoA (FIG. 2B) measured in the cells treated with negative control (a) or potassium hydroxycitrate (2-HC) (b). * * $P<0.01$; * * * * $P<0.0001$ between selected relevant comparisons.
FIG. 2C is a graph showing ChIP-PCR quantification (% enhancer enrichment) of H3K9Ac deposition at the IFN-γ locus in the cells treated with negative control (a) or potassium hydroxycitrate (2-HC) (b). * $P<0.05$.

Cytoplasmic citrate and cytoplasmic AcCoA were quantified following treatment of cells with potassium hydroxycitrate or negative control. The negative control was cell medium without potassium hydroxycitrate. The results are shown in FIGS. 2A-2B. Consistent with a model in which nucleo-cytoplasmic AcCoA concentration determines T cell function, it was discovered that potassium hydroxycitrate exposure resulted in citrate accumulation and depletion of cytoplasmic AcCoA (FIGS. 2A-2B).

Example 2

This example demonstrates that potassium hydroxycitrate treatment reduces activating histone marks at the IFN-γ promoter in T cells.

Histone acetylation acts to disrupt DNA-histone salt bridges, allowing for a euchromatin structural organization and increased local gene transcription (Garcia-Ramirez et al., J. Biol. Chem., 270: 17923-17928 (1995)). Chromatin immunoprecipitation-sequencing and PCR (ChIP-Seq and ChIP-PCR) of Histone H3 protein acetylation at the lysine on residue 9 and 27, histone marks associated with induction of transcription, were carried out following treatment of T cells with potassium hydroxycitrate or negative control.

The results are shown in FIG. 2C. The ChIP-PCR quantification showed reduced H3K9Ac deposition at the IFN-γ locus in potassium hydroxycitrate treated cells. Thus, a reduction in activating histone marks at the IFN-γ promoter (FIG. 2C) was observed following treatment with potassium hydroxycitrate.

Example 3

This example demonstrates that potassium hydroxycitrate treatment of T cells enhances autophagy.

T cells were treated with potassium hydroxycitrate or negative control. Autophagy flux was determined by measuring the loss of green fluorescent protein (GFP) in mCherry+ populations. To evaluate autophagic flux in live cells, a dynamically fluorescent GFP-mCherry-LC3b fusion reporter system (Xu et al., Nat. Immunol., 15: 1152-1161 (2014)) was employed. Using this construct, autophagic flux is measured by the loss of GFP within the mCherry+ population as autophagosomes fuse with lysosomes, indicating either consumption of GFP-LC3b via autophagic degradation or loss of GFP intensity due to the low intra-organelle pH. An autophagy incompetent construct, with a glycine to alanine substitution at position 120 (G120A), functioned as a negative control for GFP loss.

Figure 12A:
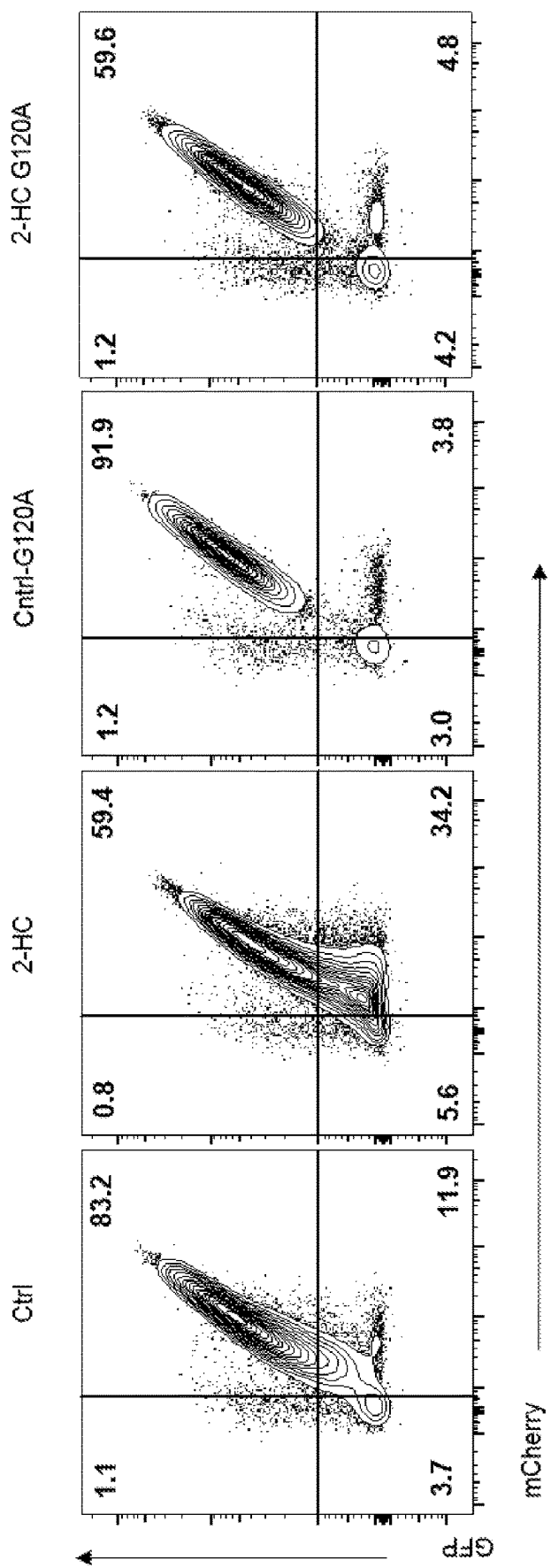
FIG. 12A shows representative flow cytometry plots of autophagy flux by measuring the loss of GFP signal and accumulation of mCherry using flow cytometry in indicated conditions. 2-HC=potassium hydroxycitrate.
Figure 12B:
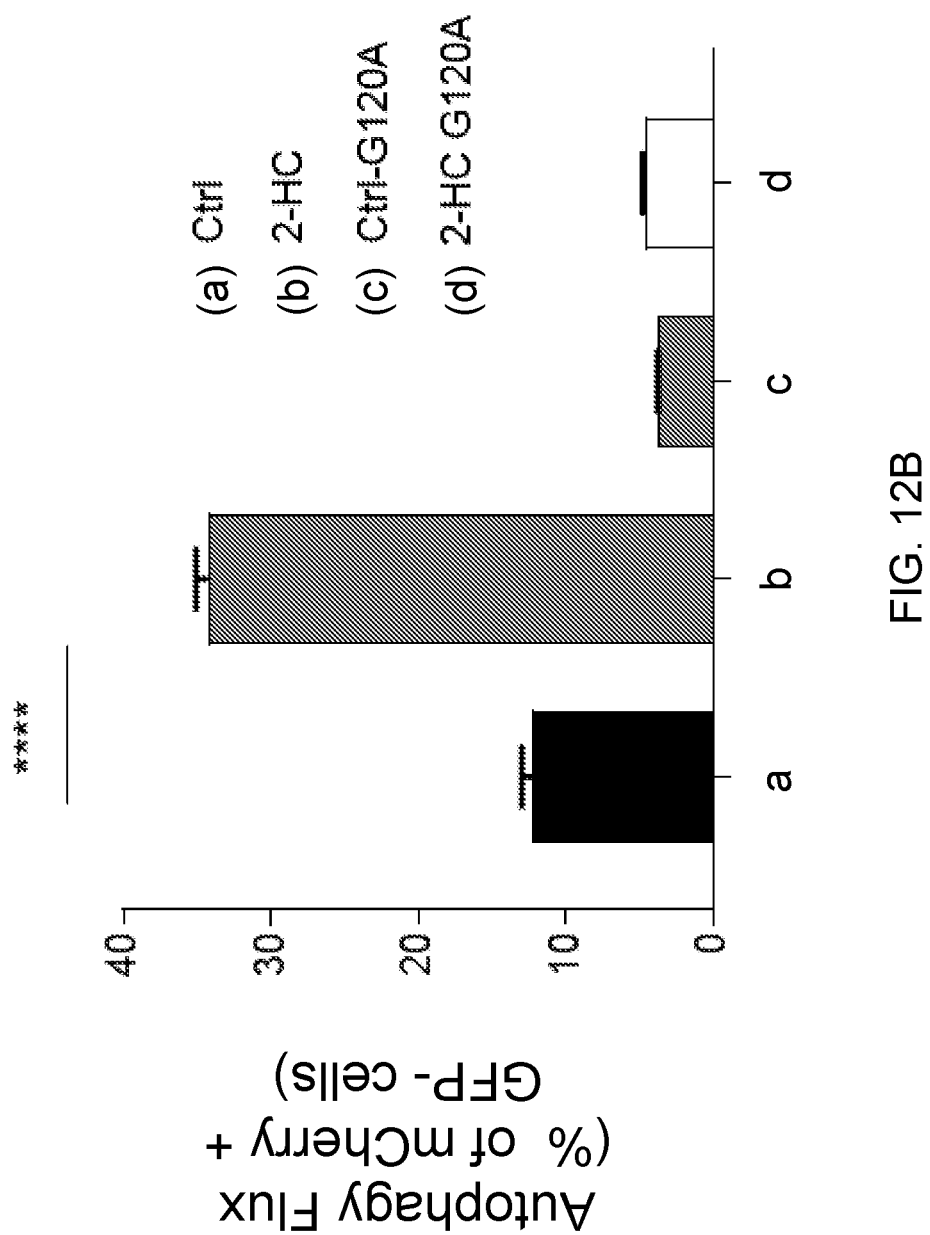
FIG. 12B is a graph showing the quantification of autophagy flux by measuring the loss of GFP signal and accumulation of mCherry using flow cytometry following treatment with control (a), potassium hydroxycitrate (2-HC) (b), control-G120A (c), or potassium hydroxycitrate G120A (d). Center values and error bars represent mean±s.e.m. * * * * P<0.0001.

The percentage of mCherry positive cells which are positive or negative for GFP were measured by flow cytometry and are shown in Table A and FIGS. 12A-12B. Enhanced autophagy was observed following potassium hydroxycitrate treatment.

TABLE A

|  | Negative control | Potassium hydroxycitrate |
| --- | --- | --- |
| GFP+ | 83.0 | 60.8 |
| GFP− | 12.1 | 33.2 |

Example 4

This example demonstrates that treating T cells with potassium hydroxycitrate blocks effector differentiation and reduces apoptosis.

CD8+ Pmel-1 T cells were activated with mhgp100 peptide for 5 days in the presence of 5 mM potassium hydroxycitrate followed by secondary stimulation with anti-CD3 (1 μg/ml) and anti-CD28 (1 μg/ml) (FIG. 7A). Cells were analyzed for surface markers or intracellular cytokines on day 10.

Representative flow cytometry analysis and quantification of CD62L vs CD44 positive cells and IFN-γ+ production in T cells cultured in control or 2-hydroxy citrate (potassium hydroxycitrate (5 mM)) are shown in Table B and FIGS. 7A and 7B. CD62L (also referred to as L-selectin) is a lymphoid homing marker and a hallmark of $T_{Mem}$ populations with the capacity for persistence. Percentages of cells with the indicated phenotype are shown in Table B.

TABLE B

|  | Negative control | Potassium hydroxycitrate |
| --- | --- | --- |
| CD44+ CD62L+ | 3.5 | 30.7 |
| IFN-γ+ | 59.3 | 14.2 |

Figure 8:
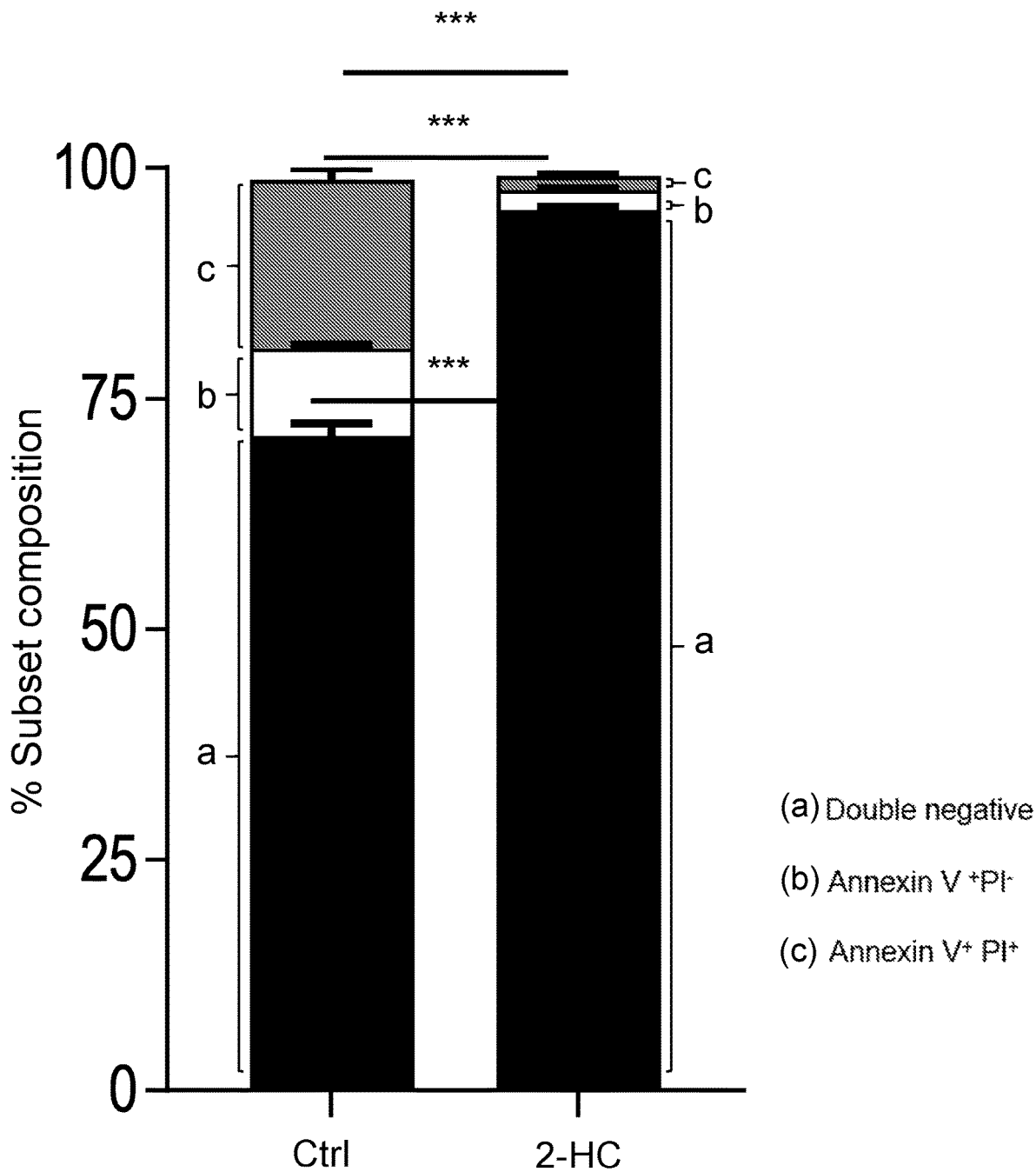
FIG. 8 is a graph showing the percentages (% subset composition) of live (Annexin V−PI−) (a), apoptotic (Annexin V+PI−) (b) and necrotic populations (Annexin V+PI+) (c) cultured in control or potassium hydroxycitrate (2-HC). Center values and error bars represent mean±s.e.m. * * * $P<0.001$.

Representative FACS data defining the percentages of live (Annexin V−PI−), apoptotic (Annexin V+PI−) and necrotic populations (Annexin V+PI+) cultured in control or potassium hydroxycitrate are provided in Table C and FIG. 8. The percentages of cells with the indicated phenotype are shown in Table C.

TABLE C

|  | Negative control | Potassium hydroxycitrate |
| --- | --- | --- |
| PI+ Annexin+ | 9.74 | 2.4 |
| PI− Annexin− | 71.0 | 95.2 |
| PI− Annexin+ | 18.1 | 1.6 |

Figure 9:
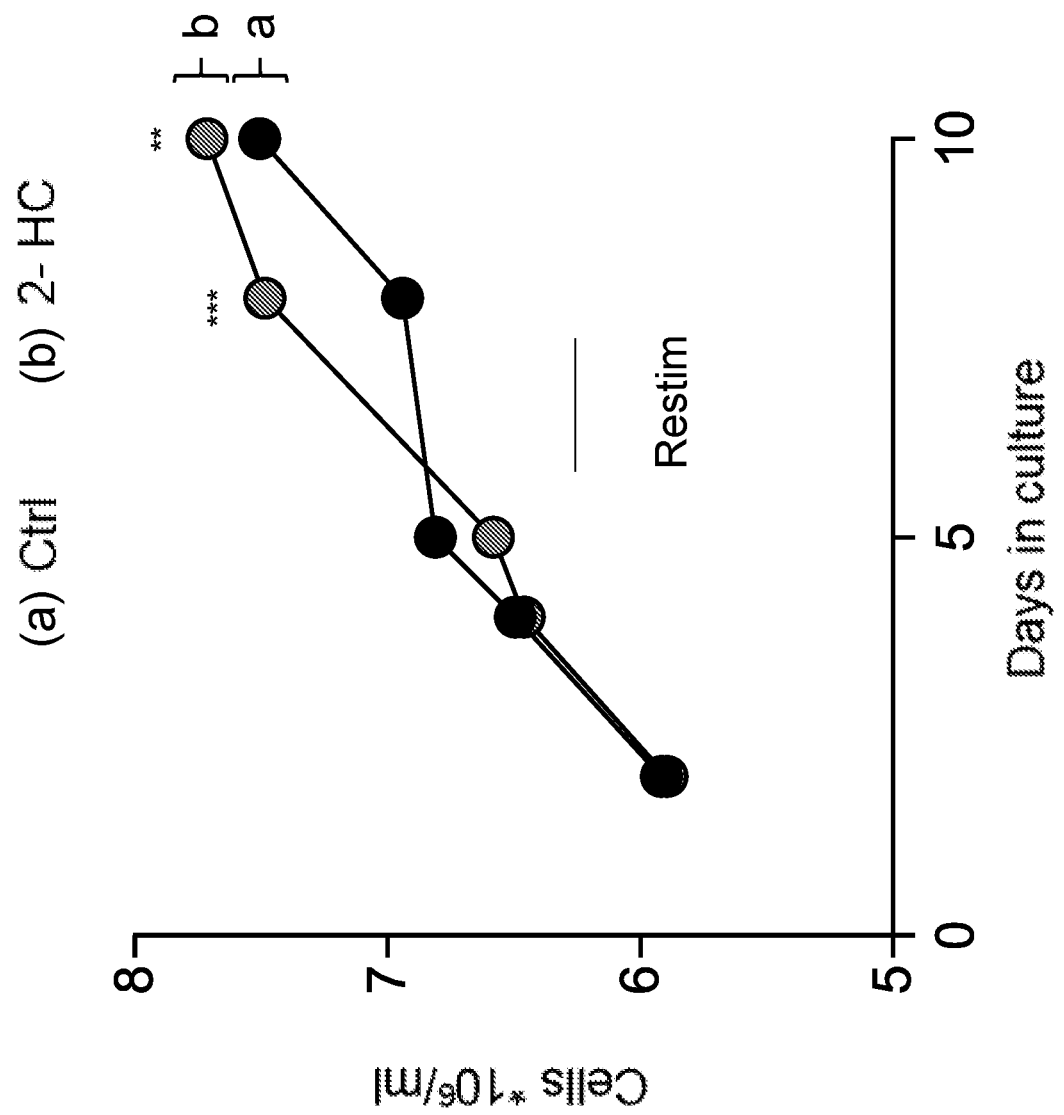
FIG. 9 is a graph showing the absolute CD8+ T cell numbers ($10^6$/ml) quantified over the course of culture (days in culture) in control (a) or potassium hydroxycitrate (2-HC) (b). Center values and error bars represent mean±s.e.m. * * $P<0.01$; * * * $P<0.001$.

Absolute CD8+ T cell numbers were quantified over the course of culture. The results are shown in FIG. 9.

The results showed a blockade of effector differentiation (Table B and FIGS. 7B-7C) and reduced cellular apoptosis (Table C and FIGS. 8-9) in the presence of potassium hydroxycitrate.

Example 5

This example demonstrates that potassium hydroxycitrate treatment of T cells reverted the acquisition of a $T_{Mem}$ marker.

T cells were treated with a combination of potassium hydroxycitrate and acetate, potassium hydroxycitrate alone, or negative control. Expression of CD62L was measured by fluorescence-activated cell sorting (FACS). The results are shown in FIGS. 3A-3B. The FACS data showed CD62L phenotype reversion by the provision of external acetate in potassium hydroxycitrate treated cells.

Figure 13:
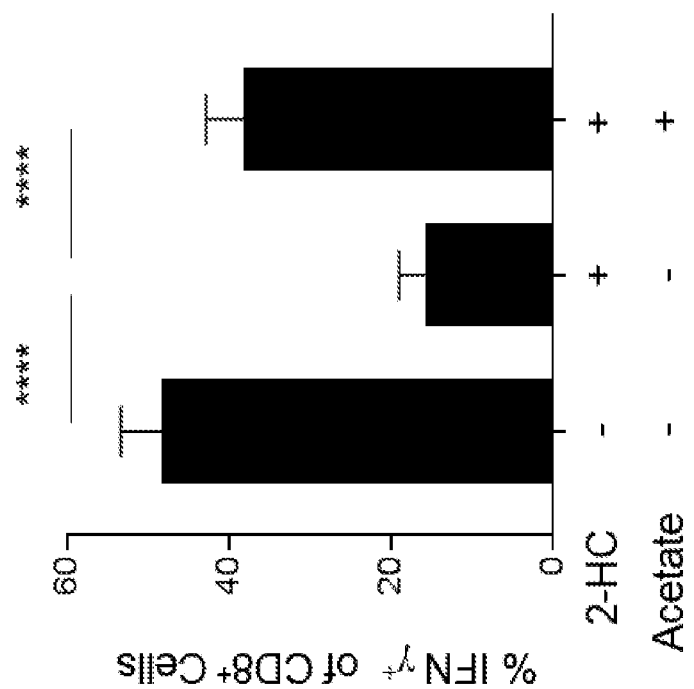
FIG. 13 is a graph showing the percentage of CD8 positive cells which were IFN-γ positive following treatment with a combination of potassium hydroxycitrate (2-HC) and acetate, potassium hydroxycitrate only, or control (neither potassium hydroxycitrate nor acetate). Center values and error bars represent mean±s.e.m. * * * * P<0.0001.

IFN-γ secretion was also measured by FACS (Table D) and quantified (FIG. 13) following treatment with control, potassium hydroxycitrate alone, or a combination of potassium hydroxycitrate and acetate. The percentages of IFN-γ positive cells are shown in Table D.

TABLE D

|  | Control | Potassium hydroxycitrate | Potassium hydroxycitrate and acetate |
| --- | --- | --- | --- |
| IFN-γ positive | 49.4 | 18.2 | 43.3 |

Figure 14:
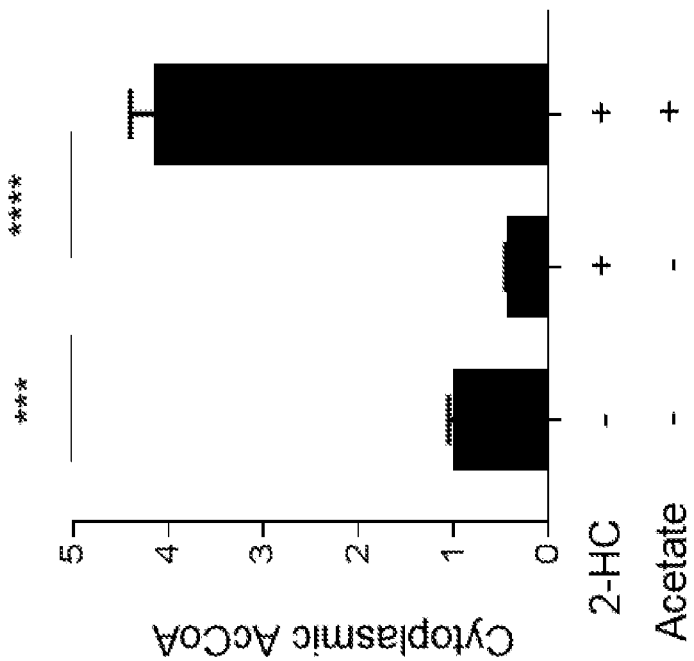
FIG. 14 is a graph showing the quantification of cytoplasmic AcCoA following treatment with a combination of potassium hydroxycitrate (2-HC) and acetate, potassium hydroxycitrate only, or control (neither potassium hydroxycitrate nor acetate). Center values and error bars represent mean±s.e.m. * * * P<0.001; * * * * P<0.0001.

Cytoplasmic AcCoA was quantified following treatment with a combination of potassium hydroxycitrate and 5 mM acetate, potassium hydroxycitrate only, or control (neither potassium hydroxycitrate nor acetate) (FIG. 14).

Ablation of autophagy was measured by immunoblot following treatment with a combination of potassium hydroxycitrate and 5 mM acetate, potassium hydroxycitrate only, or control (neither potassium hydroxycitrate nor acetate). Beta-actin was used as a control. Quantification of the autophagy flux was represented by ratio of LC3II/LC3I intensities. The results are shown in Table E.

TABLE E

| Potassium hydroxycitrate | − | + | + |
| --- | --- | --- | --- |
| Acetate | − | − | + |
| LC3II/LC3I | 0.7 | 2.1 | 0.4 |

Provision of exogenous acetate restored cytoplasmic AcCoA levels (FIG. 14) following potassium hydroxycitrate treatment and again reverted the acquisition of the $T_{Mem}$ marker CD62L, reduced autophagy, and promoted effector function (FIGS. 3A-3B and Tables D-E).

Example 6

This example demonstrates that treating T cells with potassium hydroxycitrate enhances the in vivo persistence following adoptive transfer and improves antitumor efficacy.

Figure 4:
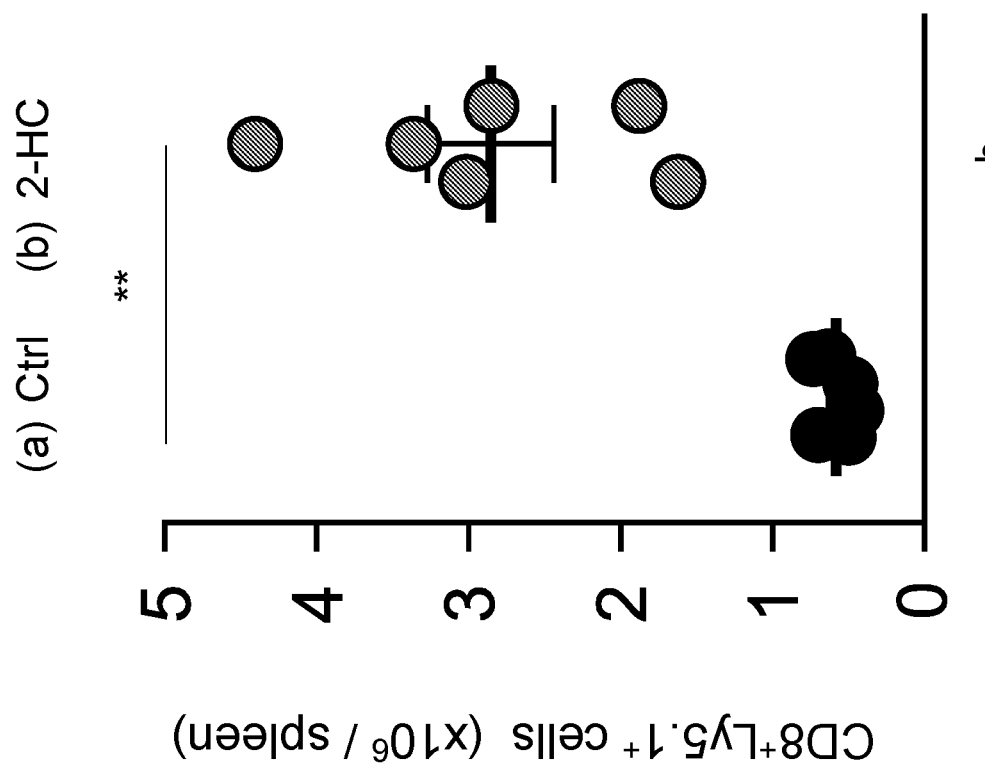
FIG. 4 is a graph showing the absolute number of transferred Ly5.1+CD8+ T cells ($\times 10^6$ per spleen) on day 7 after transfer of T cells treated with negative control (a) or potassium hydroxycitrate (2-HC) (b) into tumor-bearing mice. * * $P<0.01$.

Pmel-1 T cells were cultured in negative control (n=10) or potassium hydroxycitrate (n=10). Treated cells were transferred into mice bearing B16-mhgp100 tumors. Flow cytometry analysis and absolute number quantification of transferred Ly5.1+ CD8+ T cells in the spleen of tumor bearing mice were carried out on day 7 after transfer. Representative flow cytometry results (percentages Ly5.1+CD8+ T cells) are shown in Table F. Absolute number quantification of transferred Ly5.1+CD8+ T cells results are shown in FIG. 4.

TABLE F

|  | Negative control | Potassium hydroxycitrate |
|---|---|---|
| Ly5.1+ CD8+ T cells | 9.2 | 46.3 |

Figure 5:
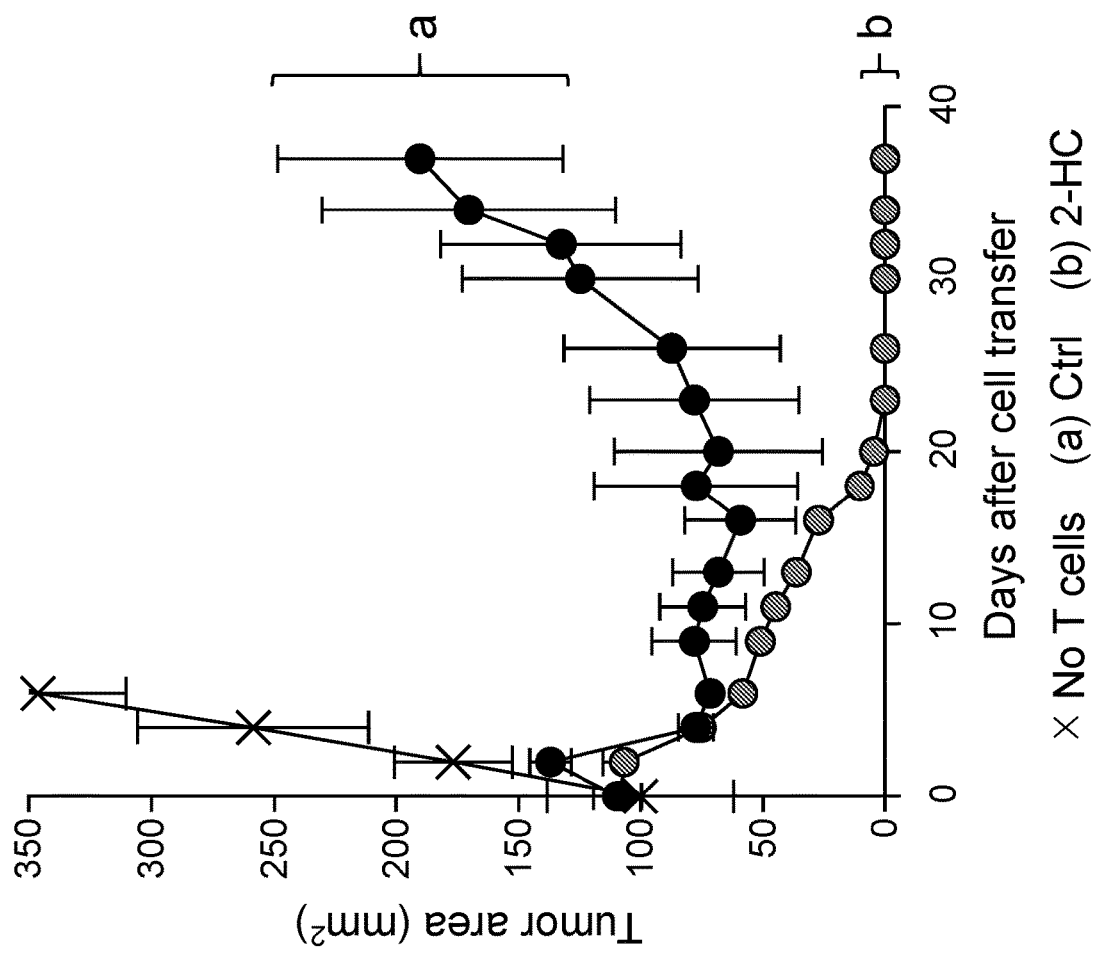
FIG. 5 is a graph showing the tumor area ($mm^2$) measured following transfer of T cells treated with negative control (a) or potassium hydroxycitrate (2-HC) (b) into tumor-bearing mice. Mice treated with no T cells (x) served as a further control. * $P<0.05$.

The anti-tumor efficacy and survival rates were measured. The results are shown in FIG. 5 (anti-tumor efficacy) and FIG. 6 (survival).

Figure 10:
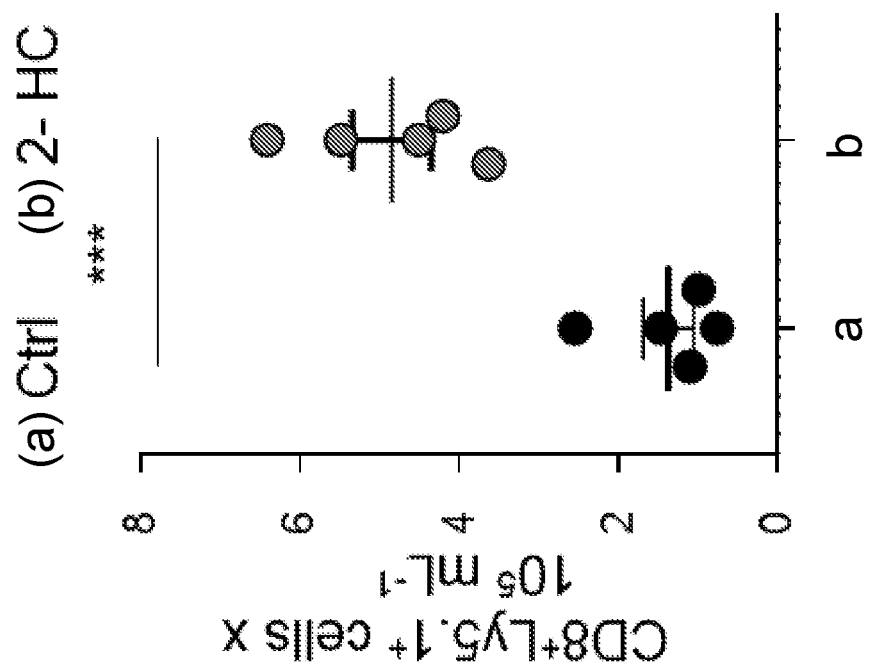
FIG. 10 is a graph showing the quantification (cells×$10^5$ $mL^{-1}$) of adoptively transferred control (a) or potassium hydroxycitrate (2-HC) (b) T cells gated on CD8+Ly5.1+. Center values and error bars represent mean±s.e.m. * * * $P<0.001$.

Adoptively transferred control or potassium hydroxycitrate T cells gated on CD8+Ly5.1+ were analyzed by FACS (Table G) and quantified (FIG. 10). Recall responses were performed by challenging the mice with vaccinia rhgp100 1×10$^7$ plaque-forming units (PFU). Representative FACS data (% of cells with the indicated phenotype) is shown in Table G.

TABLE G

|  | Negative control | Potassium hydroxycitrate |
|---|---|---|
| Ly5.1+ CD8+ T cells | 7.8 | 25.9 |

The number of B16-F10 lung metastatic nodules per lung was quantified 14 days post treatment with control (n=10) or potassium hydroxycitrate (n=10) treated T cells. The results are shown in FIG. 11.

Figure 6:
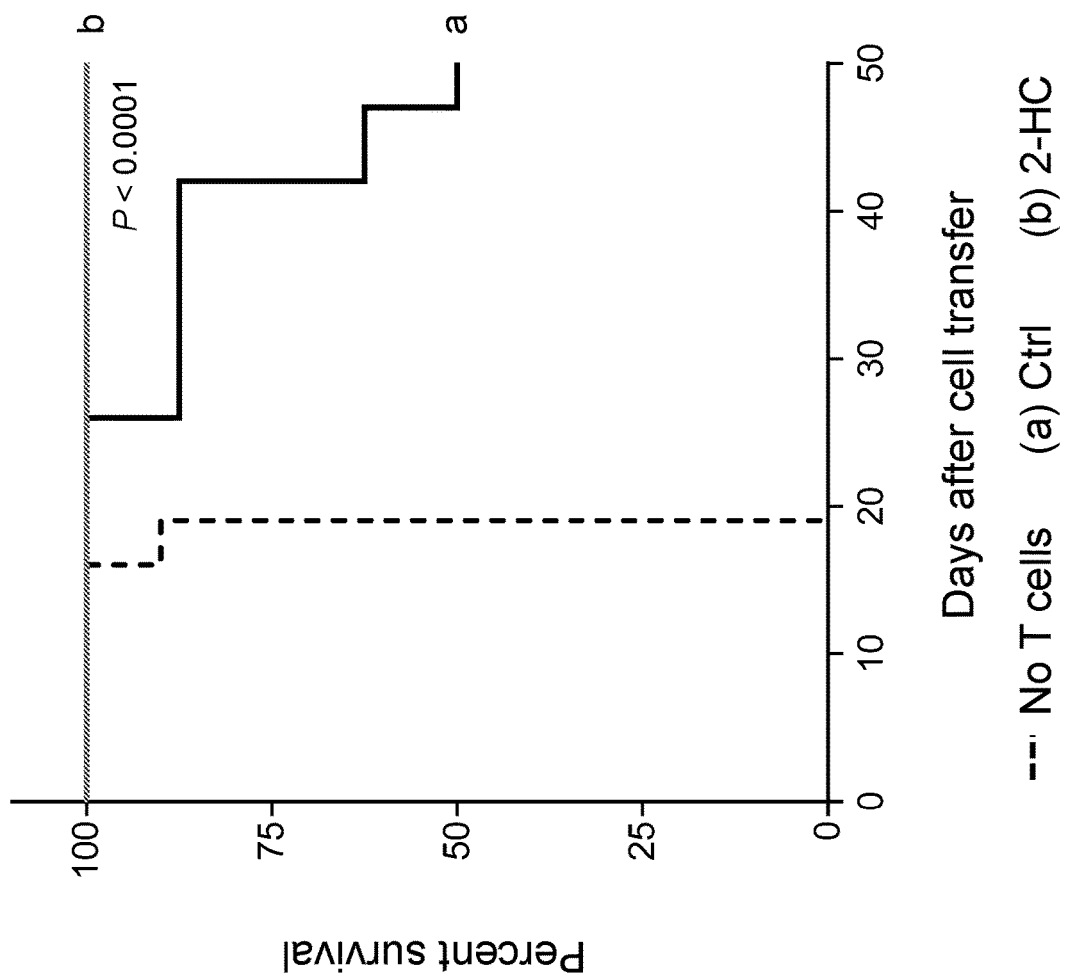
FIG. 6 is a graph showing the survival (%) of tumor-bearing mice following transfer of T cells treated with negative control (a) or potassium hydroxycitrate (2-HC) (b). Mice treated with no T cells (dotted line) served as a further control.
Figure 11:
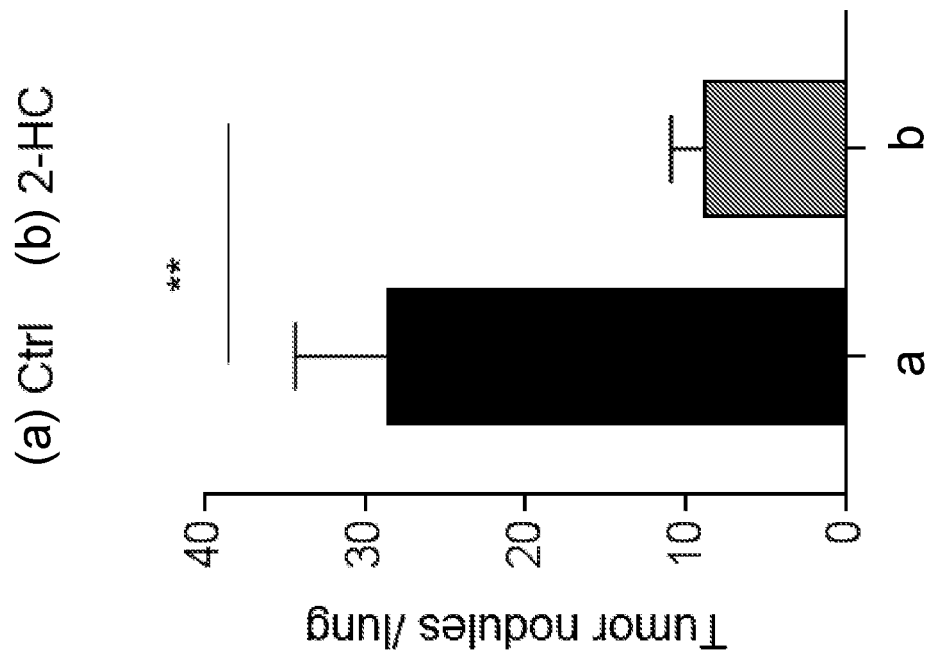
FIG. 11 is a graph showing the number of B16-F10 metastatic nodules per lung quantified 14 days post treatment with control (n=10) (a) or potassium hydroxycitrate (2-HC) (n=10) (b) treated T cells. Center values and error bars represent mean±s.e.m. * * P<0.01.

Functionally, potassium hydroxycitrate treatment enhanced in vivo persistence following adoptive transfer and improved antitumor efficacy (FIGS. 4-6, Tables F-G, and FIGS. 10-11).

Example 7

This example demonstrates that treating T cells with potassium hydroxycitrate but not citrate improves antitumor efficacy in a B16 melanoma model.

Splenocytes were isolated and cultured in control (vehicle), citrate, or potassium hydroxycitrate, restimulated, and transferred to mice bearing B16-mhgp100 tumors as shown in FIG. 15. Persistence of the transferred T cells was analyzed on day 10 in spleen. Adoptively transferred control or treated cells were analyzed for CD45.2 and CD45.1 expression by FACS and quantified (gated on CD8+Ly5.1) (Table H and FIG. 16). Representative FACS data (percentage of cells CD45.1 positive/CD45.2 negative) is shown in Table H.

TABLE H

|  | Vehicle | Citrate | Potassium hydroxycitrate |
|---|---|---|---|
| CD45.1 positive/ CD45.2 negative | 7.9 | 19.4 | 42.5 |

Anti-tumor efficacy was also measured following adoptive cell transfer. The results are shown in FIGS. 17A-17C.

As shown in Table H, FIG. 16, and FIGS. 17A-17C, treating T cells with potassium hydroxycitrate but not citrate improves antitumor efficacy in a B16 melanoma model.

Example 8

This example demonstrates that potassium hydroxycitrate treatment improves poly-functionality of human tumor infiltrating lymphocytes.

Human TIL were cultured without stimulation, in vehicle, or in potassium hydroxycitrate (2.5 or 5 mM). The cells were analyzed for the expression of tumor necrosis factor (TNF) and IL-2. Representative data are set forth in FIGS. 18A-18B and 19A-19B. As shown in FIGS. 18A-18B and 19A-19B, potassium hydroxycitrate treatment improves poly-functionality of human TIL.

Example 9

This example demonstrates that treating T cells with potassium hydroxycitrate increases expression of CD62L.

Human CD8$^+$ TILs from various histologies were cultured in the presence or absence (control) of potassium hydroxycitrate (5 mM). In brief, TILs from fresh tumor digests were subjected with 30 ng ml$^{-1}$ OKT3 to a rapid expansion protocol (REP) using irradiated peripheral blood mononuclear cells (PBMC) grown cultured in 3,000 IU ml-1 IL-2 in RPMI 1640 and AIM-V, supplemented with 5% in-house human serum 100 µg ml$^{-1}$ streptomycin and 100 µg ml$^{-1}$ penicillin, 2 mM 1-glutamine, 10 µg ml$^{-1}$ gentamicin, for approximately 14 days.

Expression of CD62L was measured by FACS. The results are shown in FIGS. 20-22B. The provision of potassium hydroxycitrate to TILs maintained relatively higher expression of the lymphoid homing marker CD62L during TIL expansion. Specifically, FIG. 20 presents representative FACS data for human TIL showing relatively higher expression of the lymphoid homing marker CD62L during TIL expansion for potassium hydroxycitrate cultured TILs as compared to control TILs (56.2 vs 66.6, 14% increase). FIG. 21 is a graph showing the percentages of cells (% of maximum) expressing CD62L following treatment with negative control or potassium hydroxycitrate. FIGS. 22A and 22B show the quantification of the data shown in FIG. 21 for CD45RO$^+$ CD62L$^+$ for two patient samples (Patient A and Patient B).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing a pharmaceutical composition, the method comprising:
   culturing isolated T cells in vitro for at least 10 days in the presence of (i) 1.0 mM to 10.0 mM hydroxycitric acid and/or a salt thereof and (ii) one or both of (a) one or more cytokines and (b) one or more non-specific T cell stimuli, wherein the salt is potassium hydroxycitrate or sodium hydroxycitrate, and wherein the T cells are from a mammal having a cancer; and
   combining the cultured T cells with a pharmaceutically acceptable carrier.

2. The method of claim 1, wherein the salt is potassium hydroxycitrate.

3. The method of claim 1, wherein the T cells have antigenic specificity for a cancer antigen.

4. The method of claim 1, further comprising introducing a nucleic acid encoding an exogenous TCR into the T cells under conditions to express the exogenous TCR by the T cells.

5. The method of claim 1, further comprising introducing a nucleic acid encoding a chimeric antigen receptor (CAR) into the T cells under conditions to express the CAR by the T cells.

6. The method of claim 1, wherein the method comprises culturing the T cells in the presence of 2.0 mM to 6.0 mM of the hydroxycitric acid and/or salt thereof.

7. The method of claim 1, wherein the method comprises nonspecifically stimulating the T cells in the presence of the hydroxycitric acid and/or salt thereof.

8. The method of claim 1, wherein the method comprises specifically stimulating the T cells in vitro in the presence of the hydroxycitric acid and/or salt thereof.

9. The method of claim 1, wherein the culturing of T cells in the presence of the hydroxycitric acid and/or salt thereof increases expression of one or more of CD62L, interleukin (IL)-2, or tumor necrosis factor (TNF) by the T cells as compared to control T cells, wherein the control T cells are identical to the T cells cultured in the presence of the hydroxycitric acid and/or salt thereof except that the control T cells are not cultured in the presence of the hydroxycitric acid and/or salt thereof.

10. The method of claim 1, wherein the T cells have antigenic specificity for a cancer neoantigen, and the method further comprises obtaining the isolated T cells by:
   screening cells obtained from the mammal for the T cells having antigenic specificity for the cancer neoantigen; and
   isolating the T cells having antigenic specificity for the cancer neoantigen from the cells obtained from the mammal.

* * * * *